US010842856B2

(12) United States Patent
Peoples et al.

(10) Patent No.: US 10,842,856 B2
(45) Date of Patent: *Nov. 24, 2020

(54) VACCINE FOR THE PREVENTION OF BREAST CANCER RELAPSE

(71) Applicant: The Henry M. Jackson Foundation for the Advancement of Military Medicine, Inc., Bethesda, MD (US)

(72) Inventors: George E. Peoples, Spring Branch, TX (US); Sathibalan Ponniah, Columbia, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/912,156

(22) Filed: Mar. 5, 2018

(65) Prior Publication Data

US 2019/0060429 A1  Feb. 28, 2019

Related U.S. Application Data

(63) Continuation of application No. 15/655,538, filed on Jul. 20, 2017, now abandoned, which is a continuation of application No. 15/376,929, filed on Dec. 13, 2016, now abandoned, which is a continuation of application No. 15/147,299, filed on May 5, 2016, now abandoned, which is a continuation of application No. 14/327,224, filed on Jul. 9, 2014, now Pat. No. 9,370,560, which is a continuation of application No. 13/534,550, filed on Jun. 27, 2012, now Pat. No. 8,796,220, which is a continuation of application No. 12/602,214, filed as application No. PCT/US2008/060044 on Apr. 11, 2008, now Pat. No. 8,222,214.

(60) Provisional application No. 60/941,524, filed on Jun. 1, 2007.

(51) Int. Cl.
| | | |
|---|---|---|
| A61K 38/00 | (2006.01) | |
| A61K 39/00 | (2006.01) | |
| A61K 38/17 | (2006.01) | |
| C07K 14/71 | (2006.01) | |
| A61K 38/19 | (2006.01) | |
| A61K 39/39 | (2006.01) | |
| A61K 9/00 | (2006.01) | |

(52) U.S. Cl.
CPC .... *A61K 39/001106* (2018.08); *A61K 9/0019* (2013.01); *A61K 38/179* (2013.01); *A61K 38/193* (2013.01); *A61K 39/00* (2013.01); *A61K 39/0011* (2013.01); *A61K 39/39* (2013.01); *C07K 14/71* (2013.01); *A61K 2039/545* (2013.01); *A61K 2039/55522* (2013.01)

(58) Field of Classification Search
CPC .................................................. A61K 39/0011
See application file for complete search history.

(56) References Cited

U.S. PATENT DOCUMENTS

| | | | |
|---|---|---|---|
| 5,846,538 A | 12/1998 | Cheever et al. | |
| 5,891,432 A | 4/1999 | Hoo | |
| 6,015,567 A | 1/2000 | Hudziak et al. | |
| 6,482,407 B2 | 11/2002 | Soo Hoo | |
| 6,514,942 B1 | 2/2003 | Ioannides et al. | |
| 6,602,510 B1 * | 8/2003 | Fikes | A61K 39/0011 424/192.1 |
| 6,664,370 B2 | 12/2003 | Cheever et al. | |
| 7,060,284 B1 | 6/2006 | Kaumaya et al. | |
| 7,247,703 B2 | 7/2007 | Cheever et al. | |
| 7,252,829 B1 * | 8/2007 | Sette | A61K 38/08 424/185.1 |
| 8,222,214 B2 * | 7/2012 | Peoples | A61K 38/179 514/19.4 |
| 8,796,220 B2 * | 8/2014 | Peoples | A61K 38/179 514/19.4 |
| 9,370,560 B2 * | 6/2016 | Peoples | A61K 38/179 |
| 2003/0022820 A1 | 1/2003 | Sherman | |
| 2003/0027766 A1 | 2/2003 | Ioannides et al. | |
| 2003/0049253 A1 | 3/2003 | Li et al. | |
| 2003/0064916 A1 | 4/2003 | Sherman | |

(Continued)

FOREIGN PATENT DOCUMENTS

| | | |
|---|---|---|
| WO | 03/076585 A2 | 9/2003 |
| WO | 2008/150577 A1 | 12/2008 |

OTHER PUBLICATIONS

Murray et al Clin. Can. Res vol. 8 p. 3407 (2002). (Year: 2002).*
Knutson et al Clin. Cancer Research vol. 8 p. 1014 (2002). (Year: 2002).*
Schijns et al Curr. Opin. Immunol. vol. 12 p. 456 (2000). (Year: 2000).*
Ezzell (J. NIH Res. 1995 7:46) (Year: 1995).*

(Continued)

*Primary Examiner* — Sheela J. Huff
(74) *Attorney, Agent, or Firm* — Nelson Mullins Riley & Scarborough LLP; Jane E. Remillard, Esq.; Cynthia L. Kanik

(57) ABSTRACT

The invention features methods to induce and maintain a protective cytotoxic T-lymphocyte response to a peptide of the HER2/neu oncogene, E75, with the effect of inducing and maintaining protective or therapeutic immunity against breast cancer in a patient in clinical remission. The methods comprise administering to the patient an effective amount of a vaccine composition comprising a pharmaceutically acceptable carrier, an adjuvant such as recombinant human GM-CSF, and the E75 peptide at an optimized dose and schedule. The methods further comprise administering an annual or semi-annual booster vaccine dose due to declining E75-specific T cell immunity. The invention also features vaccine compositions for use in the methods.

9 Claims, 17 Drawing Sheets

Specification includes a Sequence Listing.

(56) References Cited

U.S. PATENT DOCUMENTS

| | | |
|---|---|---|
| 2003/0108565 A1 | 6/2003 | Johnson et al. |
| 2003/0224036 A1 | 12/2003 | Fikes et al. |
| 2004/0018971 A1 | 1/2004 | Fikes et al. |
| 2004/0121946 A9 | 6/2004 | Fikes et al. |
| 2005/0019342 A1 | 1/2005 | Varadhachary et al. |
| 2005/0202035 A1 | 9/2005 | Subjeck et al. |
| 2005/0215501 A1 | 9/2005 | Lipford et al. |
| 2006/0014277 A1* | 1/2006 | Walke .................... C07K 14/47 435/325 |
| 2006/0014926 A1* | 1/2006 | Cassetti ............... A61K 38/162 530/300 |
| 2006/0074038 A1* | 4/2006 | Lee .................... A61K 39/0011 514/44 R |
| 2006/0088543 A1* | 4/2006 | El Halawani ...... A61K 39/0005 424/185.1 |
| 2006/0275777 A1 | 12/2006 | Waelti |
| 2007/0098776 A1 | 5/2007 | Fikes et al. |
| 2007/0148254 A1 | 6/2007 | Johnson et al. |

OTHER PUBLICATIONS

Spitler (Cancer Biotherapy, 1995, 10:1-3) (Year: 1995).*
Boon (Adv. Can. Res. 1992 58:177-210) (Year: 1992).*
Klebanoff et al, Immunol Rev vol. 239(1): 27-44 (Jan. 2011) (Year: 2011).*
American Cancer Society, "Cancer Facts & Figures 2007," http://www.cancer.org/Research/CancerFactsFigures/cancer-facts-figures-20- 07 (2007).
Amin, Asna et al., "Assessment of immunologic response and recurrence patterns among patients with clinical recurrence after vaccination with a preventive HER2/neu peptide vaccine: from US Military Cancer Institute Clinical Trials Group Study I-01 and I-02," Cancer Immunol. Immunother., vol. 57:1817-1825 (2008).
Anderson, Brett W. et al., "Peptide Priming of Cytolytic Activity to HER-2 Epitope 369-377 in Healthy Individuals," Clinical Cancer Research, vol. 6:4192-4200 (2000).
Apthera, "NeuVax (E75) for Breast Cancer," http://www.apthera.com/products.php?id=3 (2007).
Apthera, "NeuVax (E75)," http://www.apthera.com/products.php?id+2 (2007).
Apthera, "Positive Results: NeuVax (E75) Phase II Clinical Trial, About the Phase II Clinical Trial," http://www.apthera.com/neuvax.sub.-p2.sub.-results.php (2007).
Armitage, James O., "Emerging Applications of Recombinant Human Granulocyte-Macrophage Colony-Stimulating Factor," Blood, vol. 92(12):4491-4508 (1998).
Bargmann, Cornelia I. et al., "The neu oncogene encodes an epidermal growth factor receptor-related protein," Nature, vol. 319:226-230 (1986).
Barrett, Ciara et al., "Amplification of the HER2 gene in breast cancers testing 2+ weak positive by HercepTest immunohistochemistry: false: positive or false-negative immunohistochemistry?" J. Clin. Pathol., vol. 60:690-693 (2007).
Benavides, Linda C. et al., "Comparison of different HER2/neu vaccines in adjuvant breast cancer trials: implications for dosing of peptide vaccines," Expert Rev. Vaccines, vol. 10(2):201-210 (2011).
Benavides, Linda C. et al., "The Impact of HER2/neu Expression Level on Response to the E75 Vaccine: From U.S. Military Cancer Institute Clinical Trials Group Study I-01 and I-02," Clin. CAncer Res., vol. 15(8):2895-2904 (2009).
Bernhard, H. et al., "Vaccination against the HER-2/neu oncogenic protein," Endocrine-Related Cancer, vol. 9:33-44 (2002).
Bishop, Philippe C. et al., "Differential sensitivity of cancer cells to inhibitors of the epidermal growth factor receptor family," Oncogene, vol. 21:119-127 (2002).
Brossart, Peter et al., "Her-2/neu-derived Peptides Are Tumor-associated Antigens Expressed by Human Renal Cell and Colon Carcinoma Lines and Are Recognized by in Vitro Induced Specific Cytotoxic T Lymphocytes," Cancer Research, vol. 58:732-736 (1998).

Brossart, Peter et al., "Induction of cytotoxic T-lymphocyte responses in vivo after vaccinations with peptide-pulsed dendritic cells," Blood, vol. 96(9):3102-3108 (2000).
Carmichael, Mark et al., "Clinical and immunologic effects of a HER2/neu (E75) peptide vaccine booster series in previously vaccinated breast cancer patients," 99th AACR Annual Meeting, Abstract No. 2832 (2008).
Carter, Darrick et al., "Induction of Cancer Immunity by Targeted Hydrophobic Ladders in the Tumor Antigen," Immunotherapy of Cancer, vol. 15(5):A1200, Abstract No. 946.IB (2001).
Cobleigh, M.A. et al., "Efficacy and Safety of Herceptin (Humanized Anti-HER2 Antibody) as a Single Agent in 222 Women with HER2 Overexpression Who Relapsed Following Chemotherapy for Metastatic Breast Cancer," Proceedings of the ASCO, vol. 17:97a, Abstract No. 376 (1998).
Cortez-Gonzalez, Xochtil et al., "Telomerase immunity from bench to bedside: round one," Journal of Translational Medicine, vol. 5(12):1-17 (2007).
De Petris, Luigi et al., "Correlation between HLA-A2 Gene Frequency, Latitude, Ovarian and Prostate Cancer Mortality Rates," Medical Oncology, vol. 21(1):49-52 (2004).
Dehqanzada, Zia A. et al., "Assessing serum cytokine profiles in breast cancer patients receiving a HER2/neu vaccine using Luminex technology," Oncology Reports, vol. 17:687-694 (2007).
Delisi, Charles et al., "T-cell antigenic sites tend to be amphipathic structures," Proc. Natl. Acad. Sci. USA, vol. 82:7048-7052 (1985).
Disis, Mary L. et al., "Delayed-Type Hypersensitivity Response Is a Predictor of Peripheral Blood T-Cell Immunity after HER-2/neu Peptide Immunization," Clinical Cancer Research, vol. 6:1347-1350 (2000).
Disis, Mary L. et al., "Existent T-Cell and Antibody Immunity to HER-2/neu Protein in Patients with Breast Cancer," Cancer Research, vol. 54:16-20 (1994).
Disis, Mary L. et al., "Generation of Immunity to the HER-2/neu Oncogenic Protein in Patients with Breast and Ovarian Cancer Using a Peptide-based Vaccine," Clinical Cancer Research, vol. 5:1289-1297 (1999).
Disis, Mary L. et al., "Generation of T-Cell Immunity to the HER-2/neu Protein After Active Immunization With HER-2/neu Peptide-Based Vaccines," Journal of Clinical Oncology, vol. 20(11):2624-2632 (2002).
Disis, Mary L. et al., "Granulocyte-Macrophage Colony-Stimulating Factor: An Effective Adjuvant for Protein adn Peptide-Based Vaccines," Blood, vol. 88(1):202-210 (1996).
Disis, Mary L. et al., "HER-2/neu Oncogenic Protein: Issues in Vaccine Development," Critical Reviews in Immunology, vol. 18:37-45 (1998).
Disis, Mary L. et al., "In Vitro Generation of Human Cytolytic T-Cells Specific for Peptides Derived from the HER-2/neu Protooncogene Protein," Cancer Research, vol. 54:1071-1076 (1994).
Disis, Mary L. et al., "Peptide-Based, but Not Whole Protein, Vaccines Elicit Immunity to HER-2/neu, an Oncogenic Self-Protein," The Journal of Immunology, vol. 156:3151-3158 (1996).
Dranoff, Glenn et al., "Vaccination with irradiated tumor cells engineered to secrete murine granulocyte-macrophage colony-stimulating factor stimulates potent, specific, and long-lasting anti-tumor immunity," Proc. Natl. Acad. Sci. USA, vol. 90:3539-3543 (1993).
Engelhard, Victor H., "Structure of Peptides Associated with Class I and Class II MHC Molecules," Annu. Rev. Immunol., vol. 12:181-207 (1994).
Engelhorn, Manuel E. et al., "Mechanisms of Immunization Against Cancer Using Chimeric Antigens," Molecular Therapy, vol. 16(4):773-781 (2008).
Fisk, Bryan et al., "Identification of an Immunodominant Peptide of HER-2/neu Protooncogene Recognized by Ovarian Tumor-specific Cytotoxic T Lymphocyte Lines," J. Exp. Med., vol. 181:2109-2117 (1995).
Fisk, Bryan et al., "Oligopeptide Induction of a Cytotoxic T Lymphocyte Response to HER-2/neu Proto-oncogene in Vitro," Cellular Immunology, vol. 157:415-427 (1994).
Gandey, Allison, "Breast Cancer Vaccine May Prevent Recurrence," http://www.medscape.com/viewarticle/549506 (2006).

(56) References Cited

OTHER PUBLICATIONS

Gates, Jeremy D. et al., "Longterm Followup Assessment of a HER2/neu Peptide (E75) Vaccine for Prevention of Recurrence in High-Risk Prostate Cancer Patients," J. Am. Coll. Surg., vol. 208:193-201 (2009).
Gillogly, M.A. et al., "Induction of Immunity to HER-2 by TCR Directed Variants of the CTL Epitope E75," The FASEB Journal, vol. 14(6):A1139, Abstract No. 147.18 (2000).
Glantz, Michael J. et al., "A Randomized Controlled Trial Comparing Intrathecal Sustained-release Cytarabine (DepoCyt) to Intrathecal Methotrexate in Patients with Neoplastic Meningitis from Solid Tumors," Clinical Cancer Research, vol. 5:3394-3402 (1999).
Holmes, Jarrod P. et al., "Optimal Dose and Schedule of an HER-2/neu (E75) Peptide Vaccine to Prevent Breast Cancer Recurrence, From US Military Cancer Institute Clinical Trials Group Study I-01 and I-02," Cancer, vol. 113:1666-1675 (2008).
Hudson, J. Michael et al., "Growth and Antigen Recognition of Tumor-Infiltrating Lymphocytes from Human Breast Cancer," Journal of Interferon and Cytokine Research, vol. 18:529-536 (1998).
Hueman, Matthew T. et al., "Analysis of naive and memory CD4 and CD8 T cell populations in breast cancer patients receiving a HER2/neu peptide (E75) and GM-CSF vaccine," Cancer Immunol. Immunother., vol. 56:135-146 (2007).
Hueman, Matthew T. et al., "Clinical trial results of a HER2/neu peptide (E75) vaccine in preventing recurrence in node positive breast cancer patients," Proc. Amer. Assoc. Cancer Res., vol. 45:325 (2004).
Hueman, Matthew T. et al., "Phase I Clinical Trial of a HER-2/neu Peptide (E75) Vaccine for the Prevention of Prostate-Specific Antigen Recurrence in High-Risk Prostate Cancer Patients," Clin. Cancer Res., vol. 11 (20):7470-7479 (2005).
Inaba, Kayo et al., "Generation of Large Numbers of Dendritic Cells from Mouse Bone Marrow Cultures Supplemented with Granulocyte/Macrophage Colony-stimulating Factor," J. Exp. Med., vol. 176:1693-1702 (1992).
Inaba, Kayo et al., "Identification of Proliferating Dendritic Cell Precursors in Mouse Blood," J. Exp. Med., vol. 175:1157-1167 (1992).
International Search Report for Application No. PCT/US08/60044, dated Aug. 18, 2008.
Ioannides, C.G. et al., "CTL Clones Isolated from Ovarian Tumor Infiltrating Lymphocytes Can Recognize Peptides with Sequences Corresponding to the HER2/neu Gene Product," The FASEB Journal, vol. 6(4):A1404, Abstract No. 2711 (1992).
Ioannides, C.G. et al., "Cytotoxic T-Cell Clones Isolated from Ovarian Tumour Infiltrating Lymphocytes Recognize Common Determinants on Non-Ovarian Tumour Clones," Scand. J. Immunol., vol. 37:413-424 (1993).
Ioannides, Constantin G. et al., "Cytotoxic T Cells from Ovarian Malignant Tumors Can Recognize Polymorphic Epithelial Mucin Core Peptides," The Journal of Immunology, vol. 151(7):3693-3703 (1993).
Woll, Michael M. et al., "Direct Measurement of Peptide-Specific CD8+ T Cells Using HLA-A2:Ig Dimer for Monitoring the In Vivo Immune Response to a HER2/neu Vaccine in Breast and Prostate Cancer Patients," Journal of Clinical Immunology, vol. 24(4):449-461 (2004).
World Health Organization, "Cancer," http://www.who.int/mediacentre/factsheets/fs297/en/ (2012).
Yoshino, Ichiro et al., "Association of HER2/neu Expression with Sensitivity to Tumor-Specific CTL in Human Ovarian Cancer," Journal of Immunology, vol. 152:2393-2400 (1994).
Zaks, Tal Z. et al., "Immunization with a Peptide Epitope (p369-377) from HER-2/neu Leads to Peptide-specific Cytotoxic T Lymphocytes That Fail to Recognize HER-2/neu+ Tumors," Cancer Research, vol. 58:4902-4908 (1998).
Zhang, Jian-Ying et al., "Enhancement of Antibody Detection in Cancer Using Panel of Recombinant Tumor-associated Antigens," Cancer Epidemiology, Biomarkers & Prevention, vol. 12:136-143 (2003).

Ioannides, Constantin G. et al., "Cytotoxic T Cells Isolated from Ovarian Malignant Ascites Recognize a Peptide Derived from the HER-2/neu Proto-oncogene," Cellular Immunology, vol. 151:225-234 (1993).
Ioannides, Constantin G. et al., "T-Cell Recognition of Oncogene Products: A New Strategy for Immunotherapy," Molecular Carcinogenesis, vol. 6:77-82 (1992).
Karan, D. et al., "Prostate cancer: genes, environment, immunity and the use of immunotherapy," Prostate Cancer and Prostatic Disease, vol. 11:230-236 (2008).
Khoo, Steven et al., "HER2/neu vaccines in breast cancer," Women's Health, vol. 2(2):217-223 (2006).
Knutson, Keith L. et al., "Expansion of HER2/neu-Specific T Cells Ex Vivo Following Immunization with a HER2/neu Peptide-Based Vaccine," Clinical Breast Cancer, vol. 2(1):73-79 (2001).
Knutson, Keith L. et al., "Immunization of Cancer Patients with a HER-2/neu, HLA-A2 Peptide, p369-377, Results in Short-lived Peptide-specific Immunity," Clinical Cancer Research, vol. 8:1014-1018 (2002).
Knutson, Keith L. et al., "Immunization with a HER-2/neu helper peptide vaccine generates HER-2/neu CD8 T-cell immunity in cancer patients," The Journal of Clinical Investigation, vol. 107(4):477-484 (2001).
Kono, Koji et al., "Dendritic Cells Pulsed with HER-2/neu-derived Peptides Can Induce Specific T-Cell Responses in Patients with Gastric Cancer," Clinical Cancer Research, vol. 8:3394-3400 (2002).
Kushner, Brian H. et al., "GM-CSF Enhances 3F8 Monoclonal Antibody-Dependent Cellular Cytotoxicity Against Human Melanoma and Neuroblastoma," Blood, vol. 73(7):1936-1941 (1989).
Lee, Jeffrey E. et al., "Association of Gastric Adenocarcinoma With the HLA Class II Gene DQB1 0301," Gastroenterology, vol. 111:426-432 (1996).
Lee, Jeffrey E., "Factors Associated With Melanoma Incidence and Prognosis," Seminars in Surgical Oncology, vol. 12:379-385 (1996).
Leukine (sargramostim) prescribing information: http://berlex.bayerhealthcare.com/html/products/pi/Leukine.sub.-PI.pdf (2008).
Leukine package insert: http://patient.cancerconsultants.com/druginserts/Sargramostim.pdf (2002).
Ludovini, V. et al., "Evaluation of serum HER2 extracellular domain in early breast cancer patients: correlation with clinicopathological parameters and survival," Annals of Oncology, vol. 19:883-890 (2008).
Lustgarten, J. et al., "Generation of Xenogeneic Cytotoxic T Cells from Peptides Derived from the HER-2/neu Protooncogene," 9th International Congress of Immunology, p. 663, Abstract No. 3935 (1995).
Menendez, Javier A. et al., "Trastuzumab in Combination With Heregulin-Activated Her-2 (erbB-2) Triggers a Receptor-Enhanced Chemosensitivity Effects in the Absence of Her-2 Overexpression," Journal of Clinical Oncology, vol. 24(23):3735-3746 (2006).
Meyer Zum Buschenfelde, Christian et al., "Generation of Tumor-Reactive CTL Against the Tumor-Associated Antigen HER2 Using Retrovirally Transduced Dendritic Cells Derived from CD34 Hemopoietic Progenitor Cells," The Journal of Immunology, vol. 165:4133-4140 (2000).
Mincey, Betty A. et al., "Adjuvant Therapy for Breast Cancer: Recommendations for Management Based on Consensus Review and Recent Clinical Trials," The Oncologist, vol. 7:246-250 (2002).
Mincey, Betty A., "Genetics and the Management of Women at High Risk for Breast Cancer," The Oncologist, vol. 8:466-473 (2003).
Mittendorf, Elizabeth A. et al., "Breast cancer vaccine: ongoing National Cancer Institute-registered clinical trials," Expert Rev. Vaccines, vol. 10(6):755-774 (2011).
Mittendorf, Elizabeth A. et al., "Clinical Trial Results of the HER-2/neu (E75) Vaccine to Prevent Breast Cancer Recurrence in High-Risk Patients," Cancer, DOI: 10.1002/cncr.26574 (2011).
Mittendorf, Elizabeth A. et al., "The E75 HER2/neu peptide vaccine," Cancer Immunol. Immunother., vol. 57:1511-1521 (2008).
Mittendorf, Elizabeth A. et al., "Vaccination with a HER2/neu peptide induces intra- and inter-antigenic epitope spreading in patients with early stage breast cancer," Surgery, vol. 139:407-418 (2006).

(56) References Cited

OTHER PUBLICATIONS

Mohsin, Syed K. et al., "Neoadjuvant Trastuzumab Induces Apoptosis in Primary Breast Cancers," Journal of Clinical Oncology, vol. 23(11):2460-2468 (2005).

Moon, YW et al., "Different criteria for HER2 positivity by IHC can be applied in post-chemotherapy specimens in determining HER2 as a prognosticator in locally advanced breast cancer," Breast Cancer Research Treatment, 104(1):31-37 (2007).

Murray, James L. et al., "Toxicity, Immunogenicity, and Induction of E75-specific Tumor-lytic CTLs by HER-2 Peptide E75 (369-377) Combined with Granulocyte Macrophage Colony-stimulating Factor in HLA-A2+ Patients with Metastatic Breast and Ovarian Cancer," Clinical Cancer Research, vol. 8:3407-3418 (2002).

National Institutes of Health, "NIH Consensus Statement," vol. 17(4) (2000).

Paik, S. et al., "Benefit from adjuvant trastuzumab may not be confined to patients with IHC 3+ and/or FISH-positive tumors: Central testing results from NSABP B-31," Journal of Clinical Oncology, 2007 ASCO Annual Meeting Proceedings (Post-Meeting Edition), vol. 25(18S): 511, (2007) XP055262219, Retrieved from the Internet: <URL:http://meeting.ascopubs.org/cgi/>content/short/25/18_suppl/511 [retrieved on Apr. 1, 2016].

Parmiani, G. et al., "Opposite immune functions of GM-CSF administered as vaccine adjuvant in cancer patients," Annals of Oncology, vol. 18:226-232 (2007).

Peoples, G.E. et al., "Combined clinical trial results of a HER2/neu (E75) vaccine for prevention of recurrence in high-risk breast cancer patients," 29th Annual San Antonio Breast Cancer Symposium, Breast Cancer Research and Treatment, vol. 100(Suppl. 1):S6 (2006).

Peoples, George E. et al., "Breast and ovarian cancer-specific cytotoxic T lymphocytes recognize the same HER2/neu-derived peptide," Proc. Natl. Acad. Sci. USA, vol. 92:432-436 (1995).

Peoples, George E. et al., "Clinical Trial Results of a HER2/neu (E75) Vaccine to Prevent Recurrence in High-Risk Breast Cancer Patients," Journal of Clinical Oncology, vol. 23(30):7536-7545 (2005).

Peoples, George E. et al., "Combined Clinical Trial Results of a HER2/neu (E75) Vaccine for the Prevention of Recurrence in High-Risk Breast Cancer Patients: U.S. Military Cancer Institute Clinical Trials Group Study I-01 and I-02," Clin. Cancer Res., vol. 14(3):797-803 (2008).

Perkins, Raymond C. et al., "Effects of Continuous High Dose rhGM-CSF Infusion on Human Monocyte Activity," American Journal of Hematology, vol. 43:279-285 (1993).

Pupa, Serenella M. et al., "Antibody Response against the c-erbB-2 Oncoprotein in Breast Carcinoma Patients," Cancer Research, vol. 53:5864-2866 (1993).

Rice, Jason et al., "DNA vaccines: precision tools for activating effective immunity against cancer," Nature Reviews Cancer, vol. 8:108-120 (2008).

Ridolfi, R. et al., "HER-2/neu Testing in Breast Carcinoma: A Combined Immunohistochemical and Fluorescence In Situ Hybridization Approach," Modern Pathology, vol. 13(8): 866-873, (2000) XP055262216, GB ISSN: 0893-3952, DOI: 10.1038/modpathol.3880154.

Ross, Jeffrey S. et al., "Prognostic Significance of HER-2/neu Gene Amplification Status by Fluorescence in Situ Hybridization of Prostate Carcinoma," Cancer, vol. 79:2162-2170 (1997).

Rothbard, Jonathan B. et al., "A sequence pattern common to T cell epitopes," The EMBO Journal, vol. 7 (1):93-100 (1988).

Saito, Takeshi et al., "Therapeutic Potential of a Reduced-Intensity Preparative Regimen for Allogeneic Transplantation with Cladribine, Busulfan, and Antithymocyte Globulin against Advanced/Refractory Acute Leukemia/Lymphoma," Clinical Cancer Research, vol. 8:1014-1020 (2002).

Scardino, Antonio et al., "A Polyepitope DNA Vaccine Targeted to Her-2/ErbB-2 Elicits a Broad Range of Human and Murine CTL Effectors to Protect against Tumor Challenge," Cancer Res., vol. 67(14):7028-7036 (2007).

Schaed, Susanne G. et al., "T-Cell Responses against Tyrosinase 368-376(370D) Peptide in HLA A0201+ Melanoma Patients: Randomized Trial Comparing Incomplete Freund's Adjuvant, Granulocyte Macrophage Colony-stimulating Factor, and QS-21 Immunological Adjuvants," Clinical Cancer Research, vol. 8:967-972 (2002).

Seidman, Andrew, "Developing a Breast Cancer Vaccine: Works in Progress," http://www.medscape.com/viewarticle/428777 (1999).

Signoretti, Sabina et al., "Her-2-neu Expression and Progression Toward Androgen Independence in Human Prostate Cancer," Journal of the National Cancer Institute, vol. 92(23):1918-1925 (2000).

Skacel, Marek et al., "Aneusomy of Chromosomes 7, 8, and 17 and Amplification of HER-2/neu and Epidermal Growth Factor Receptor in Gleason Score 7 Prostate Carcinoma: A Differential Fluorescent in Situ Hybridization Study of Gleason Pattern 3 and 4 Using Tissue Microarray," Hum. Pathol., vol. 32(12):1392-1397 (2001).

Stojadinovic, Alexander et al., "Quantification and Phenotypic Characterization of Circulating Tumor Cells for Monitoring Response to a Preventive HER2/neu Vaccine-Based Immunotherapy for Breast Cancer: A Pilot Study," Annals of Surgical Oncology, vol. 14(12):3359-3368 (2007).

Trastuzumab prescribing information: http://www.herceptin.com/pdf/herceptin-prescribing.pdf (2010).

Tubbs, R.R. et al., "Discrepancies in Clinical Laboratory Testing of Eligibility for Trastuxumab Therapy: Apparent Immunohistochemical False-Positives Do Not Get the Message," Journal of Clinical Oncology, vol. 19(10):2714-2721 (2001).

Tuttle, Todd M. et al., "Proliferative and Cytokine Responses to Class II HER-2/neu-associated Peptides in Breast Cancer Patients," Clinical Cancer Research, vol. 4:2015-2024 (1998).

Wolff, Antonio C. et al., "American Society of Clinical Oncology/College of American Pathologists Guideline Recommendations for Human Epidermal Growth Factor Receptor 2 Testing in Breast Cancer," Arch. Pathol. Lab. Med., vol. 131:18-43 (2007).

U.S. Appl. No. 14/327,224, filed Jul. 9, 2014, George E. Peoples.
U.S. Appl. No. 13/534,550, filed Jun. 27, 2012, George E. Peoples.
U.S. Appl. No. 12/602,214, filed Nov. 30, 2009, George E. Peoples.
U.S. Appl. No. 14/327,224, May 20, 2016.
U.S. Appl. No. 14/327,224, May 16, 2016.
U.S. Appl. No. 14/327,224, Feb. 4, 2016.
U.S. Appl. No. 14/327,224, Jul. 8, 2015.
U.S. Appl. No. 13/534,550, Jun. 23, 2014.
U.S. Appl. No. 13/534,550, Dec. 5, 2013.
U.S. Appl. No. 12/602,214, Mar. 19, 2012.
U.S. Appl. No. 12/602,214, Nov. 15, 2011.

* cited by examiner

SEQUENCE LISTING

<160> NUMBER OF SEQ ID NOS: 5

<210> SEQ ID NO 1
<211> LENGTH: 1225
<212> TYPE: PRT
<213> ORGANISM: Artificial Sequence
<220> FEATURE:
<223> OTHER INFORMATION: Synthetic construct

<400> SEQUENCE: 1

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln

-continued

```
            355                 360                 365
Val Phe Glu Thr Leu Glu Glu Ile Thr Gly Tyr Leu Tyr Ile Ser Ala
        370                 375                 380
Trp Pro Asp Ser Leu Pro Asp Leu Ser Val Phe Gln Asn Leu Gln Val
385                 390                 395                 400
Ile Arg Gly Arg Ile Leu His Asn Gly Ala Tyr Ser Leu Thr Leu Gln
                405                 410                 415
Gly Leu Gly Ile Ser Trp Leu Gly Leu Arg Ser Leu Arg Glu Leu Gly
                420                 425                 430
Ser Gly Leu Ala Leu Ile His His Asn Thr His Leu Cys Phe Val His
            435                 440                 445
Thr Val Pro Trp Asp Gln Leu Phe Arg Asn Pro His Gln Ala Leu Leu
        450                 455                 460
His Thr Ala Asn Arg Pro Glu Asp Glu Cys Val Gly Glu Gly Leu Ala
465                 470                 475                 480
Cys His Gln Leu Cys Ala Arg Gly His Cys Trp Gly Pro Gly Pro Thr
                485                 490                 495
Gln Cys Val Asn Cys Ser Gln Phe Leu Arg Gly Gln Glu Cys Val Glu
                500                 505                 510
Glu Cys Arg Val Leu Gln Gly Leu Pro Arg Glu Tyr Val Asn Ala Arg
            515                 520                 525
His Cys Leu Pro Cys His Pro Glu Cys Gln Pro Gln Asn Gly Ser Val
        530                 535                 540
Thr Cys Phe Gly Pro Glu Ala Asp Gln Cys Val Ala Cys Ala His Tyr
545                 550                 555                 560
Lys Asp Pro Pro Phe Cys Val Ala Arg Cys Pro Ser Gly Val Lys Pro
                565                 570                 575
Asp Leu Ser Tyr Met Pro Ile Trp Lys Phe Pro Asp Glu Glu Gly Ala
                580                 585                 590
Cys Gln Pro Cys Pro Ile Asn Cys Thr His Ser Cys Val Asp Leu Asp
            595                 600                 605
Asp Lys Gly Cys Pro Ala Glu Gln Arg Ala Ser Pro Leu Thr Ser Ile
        610                 615                 620
Ile Ser Ala Val Val Gly Ile Leu Leu Val Val Val Leu Gly Val Val
625                 630                 635                 640
Phe Gly Ile Leu Ile Lys Arg Arg Gln Gln Lys Ile Arg Lys Tyr Thr
                645                 650                 655
Met Arg Arg Leu Leu Gln Glu Thr Glu Leu Val Glu Pro Leu Thr Pro
                660                 665                 670
Ser Gly Ala Met Pro Asn Gln Ala Gln Met Arg Ile Leu Lys Glu Thr
            675                 680                 685
Glu Leu Arg Lys Val Lys Val Leu Gly Ser Gly Ala Phe Gly Thr Val
        690                 695                 700
Tyr Lys Gly Ile Trp Ile Pro Asp Gly Glu Asn Val Lys Ile Pro Val
705                 710                 715                 720
Ala Ile Lys Val Leu Arg Glu Asn Thr Ser Pro Lys Ala Asn Lys Glu
                725                 730                 735
Ile Leu Asp Glu Ala Tyr Val Met Ala Gly Val Gly Ser Pro Tyr Val
                740                 745                 750
Ser Arg Leu Leu Gly Ile Cys Leu Thr Ser Thr Val Gln Leu Val Thr
            755                 760                 765
Gln Leu Met Pro Tyr Gly Cys Leu Leu Asp His Val Arg Glu Asn Arg
        770                 775                 780
```

```
Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
            805                 810                 815

Ala Ala Arg Asn Val Leu Val Lys Ser Pro Asn His Val Lys Ile Thr
        820                 825                 830

Asp Phe Gly Leu Ala Arg Leu Leu Asp Ile Asp Glu Thr Glu Tyr His
    835                 840                 845

Ala Asp Gly Gly Lys Val Pro Ile Lys Trp Met Ala Leu Glu Ser Ile
850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
            885                 890                 895

Pro Ala Arg Glu Ile Pro Asp Leu Leu Glu Lys Gly Glu Arg Leu Pro
        900                 905                 910

Gln Pro Pro Ile Cys Thr Ile Asp Val Tyr Met Ile Met Val Lys Cys
    915                 920                 925

Trp Met Ile Asp Ser Glu Cys Arg Pro Arg Phe Arg Glu Leu Val Ser
930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
            965                 970                 975

Ser Leu Leu Glu Asp Asp Asp Met Gly Asp Leu Val Asp Ala Glu Glu
        980                 985                 990

Tyr Leu Val Pro Gln Gln Gly Phe Phe Cys Pro Asp Pro Ala Pro Gly
    995                 1000                1005

Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050

Asp Val Phe Asp Gly Asp Leu Gly Met Gly Ala Ala Lys Gly Leu
    1055                1060                1065

Gln Ser Leu Pro Thr His Asp Pro Ser Pro Leu Gln Arg Tyr Ser
    1070                1075                1080

Glu Asp Pro Thr Val Pro Leu Pro Ser Glu Thr Asp Gly Tyr Val
    1085                1090                1095

Ala Pro Leu Thr Cys Ser Pro Gln Pro Glu Tyr Val Asn Gln Pro
    1100                1105                1110

Asp Val Arg Pro Gln Pro Pro Ser Pro Arg Glu Gly Pro Leu Pro
    1115                1120                1125

Ala Ala Arg Pro Ala Gly Ala Thr Leu Glu Arg Pro Lys Thr Leu
    1130                1135                1140

Ser Pro Gly Lys Asn Gly Val Val Lys Asp Val Phe Ala Phe Gly
    1145                1150                1155

Gly Ala Val Glu Asn Pro Glu Tyr Leu Thr Pro Gln Gly Gly Ala
    1160                1165                1170

Ala Pro Gln Pro His Pro Pro Pro Ala Phe Ser Pro Ala Phe Asp
    1175                1180                1185
```

```
Asn Leu  Tyr Tyr Trp Asp Gln  Asp Pro Pro Glu  Arg  Gly Ala Pro
    1190             1195                 1200

Pro Ser  Thr Phe Lys Gly Thr  Pro Thr Ala Glu  Asn  Pro Glu Tyr
    1205             1210                 1215

Leu Gly  Leu Asp Val Pro Val
    1220             1225

<210> SEQ ID NO 2
<211> LENGTH: 9
<212> TYPE: PRT
<213> ORGANISM: Artificial Sequence
<220> FEATURE:
<223> OTHER INFORMATION: Synthetic construct

<400> SEQUENCE: 2

Lys Ile Phe Gly Ser Leu Ala Phe Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

Asx Ile Met Ala Ser
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic construct

<400> SEQUENCE: 4

Ser Tyr Phe Pro Glu Ile Thr His Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic construct

<400> SEQUENCE: 5

Arg Ile Ala Trp Ala Arg Thr Glu Leu
1               5
```

VACCINE FOR THE PREVENTION OF BREAST CANCER RELAPSE

CROSS-REFERENCE TO RELATED APPLICATIONS

This application is a continuation of U.S. patent application Ser. No. 15/655,538, filed Jul. 20, 2017, now abandoned, which is a continuation of U.S. patent application Ser. No. 15/376,929, filed Dec. 13, 2016, now abandoned, which is a continuation of U.S. patent application Ser. No. 15/147,299, filed May 5, 2016, now abandoned, which is a continuation of U.S. Pat. No. 9,370,560, issued Jun. 21, 2016, which is a continuation of U.S. Pat. No. 8,796,220, issued Aug. 5, 2014 which is a continuation of U.S. Pat. No. 8,222,214, issued Jul. 17, 2012, which is the U.S.C. § 371 filing of International Application Number PCT/US2008/060044, filed Apr. 11, 2008, which claims priority to, and the benefit of, U.S. Application No. 60/941,524, filed on Jun. 1, 2007. The contents of the aforementioned applications are hereby incorporated herein by reference.

SEQUENCE LISTING

The instant application contains a Sequence Listing which has been submitted in ASCII format via EFS-Web, and is hereby incorporated by reference in its entirety. Said ASCII copy, created on Mar. 5, 2018, is named RXJ-004USCN6_Sequence_Listing.txt and is 12,007 bytes in size.

STATEMENT AS TO FEDERALLY SPONSORED RESEARCH

This invention was made with government support under grant W81XWH-05-2-0053 awarded by the U.S. Army Medical Research and Material Command. The government has certain rights in the invention.

FIELD

The invention relates generally to the field of preventive and therapeutic vaccines. More specifically, the invention relates to peptide vaccines for the treatment of breast cancer and the prevention of relapse in patients in breast cancer remission.

BACKGROUND

Various publications, including patents, published applications, technical articles and scholarly articles are cited throughout the specification. Each of these cited publications is incorporated by reference herein, in its entirety and for all purposes.

Breast cancer (BCa) is the most common cancer diagnosis in women and the second-leading cause of cancer-related death among women (Ries L A G, et al. (eds). SEER Cancer Statistics Review, 1975-2003, National Cancer Institute, Bethesda, Md.). Major advances in breast cancer treatment over the last 20 years have led to significant improvement in the rate of disease-free survival (DFS). For example, therapies utilizing antibodies reactive against tumor-related antigens have been used to block specific cellular processes in order to slow disease progress or prevent disease recurrence. Despite the recent advances in breast cancer treatment, a significant number of patients will ultimately die from recurrent disease. Thus, there is a need for treatments that prevent or slow or prohibit the development of recurrent disease.

Vaccines are an attractive model for such treatments and preventions due to their ease of administration, and because of their high rate of success observed for infectious diseases. The basic concept of constructing a cancer vaccine is straightforward in theory. The development of effective cancer vaccines for solid tumors in practice, however, has met with limited success. For example, one group attempting to administer a peptide vaccine directed against metastatic melanoma observed an objective response rate of only 2.6% (Rosenberg S A et al. (2004) Nat. Med. 10:909-15).

There are many potential explanations for this low success rate (Campoli M et al. (2005) Cancer Treat. Res. 123:61-88). For example, even if an antigen is specifically associated with a particular type of tumor cell, the tumor cells can express only low levels of the antigen, or it can be located in a cryptic site or otherwise shielded from immune detection. In addition, tumors often change their antigenic profile by shedding antigens as they develop. Also contributing to the low success rate is the fact that tumor cells can express very low levels of MHC proteins and other co-stimulatory proteins necessary to generate an immune response.

Additional problems facing attempts at vaccination against tumors arise in patients with advanced-stage cancers. Such patients tend to have larger primary and metastatic tumors, and the cells on the interior of the tumor can not be accessible due to poor blood flow. This is consistent with the observation that vaccine strategies have tended to be more successful for the treatment of hematologic malignancies (Radford K J et al. (2005) Pathology 37:534-50; and, Molldrem J J (2006) Biol. Bone Marrow Transplant. 12:13-8). In addition, as tumors become metastatic, they can develop the ability to release immunosuppressive factors into their microenvironment (Campoli, 2005; and, Kortylewski M et al. (2005) Nature Med. 11:1314-21). Metastatic tumors have also been associated with a decrease in the number of peripheral blood lymphocytes, and dendritic cell dysfunction (Gillanders W E et al. (2006) Breast Diseases: A Year Book and Quarterly 17:26-8).

While some or all of these factors can contribute to the difficulty in developing an effective preventative or therapeutic vaccine, the major underlying challenge is that most tumor antigens are self antigens or have a high degree of homology with self antigens, and are thus expected to be subject to stringent immune tolerance. Thus, it is clear that many peptide-based cancer vaccines, with or without immune-stimulating adjuncts, can be doomed to only limited success in clinical practice due to low immunogenicity and lack of specificity.

Prototype breast cancer vaccines based on single antigens have been moderately successful in inducing a measurable immune response in animal experiments and in clinical tests with breast cancer patients. The observed immune response, however, has not translated into a clinically-significant protective immunity against resurgence of disease put in remission by standard surgery and chemotherapy. Thus, novel vaccine approaches are needed to further improve recurrence rates and overall survival among BCa patients.

Preferred vaccine epitopes are those that are expressed exclusively, or at least at increased levels by a neoplasm. HER2/neu is a proto-oncogene expressed in many epithelial malignancies (Slamon D J et al. (1989) Science 244:707-12). Gene amplification and overexpression of the HER2/neu protein is found in 20-25% of BCa, and its excess presence is an indicator of poor prognosis (Pritchard K I et al. (2006) N. Engl. J. Med. 354:2103-11). HER2/neu has been studied fairly extensively, and several immunogenic peptides have been identified from this protein. One such peptide is termed E75, and corresponds to amino acids 369-377 of HER2/neu (SEQ ID NO:1) (U.S. Pat. No. 6,514,942).

Attempts have been made to utilize E75 as an anti-cancer vaccine, for example, as a single peptide vaccine combined with different immunoadjuvants (Zaks T Z et al. (1998) Cancer Res. 58:4902-8; Knutson K L et al. (2002) Clin. Cancer Res. 8:1014-8; and, Murray J L et al. (2002) Clin. Cancer Res. 8:3407-18); loaded on to autologous dendritic cells and reinfused (Brossart P et al. (2000) Blood 96:3102-8; and, Kono K et al. (2002) Clin. Cancer Res. 8:3394-3400); or embedded in longer peptides capable of binding HLA class II molecules in order to recruit CD4 helper T-cells (Disis M L et al. (1999) Clin. Cancer Res. 5:1289-97; and, Disis M L et al. (2002) J. Clin. Oncol. 20:2624-32). Each approach has stimulated an E75-specific cytotoxic T cell-mediated immune response, but has not demonstrated a clinically significant therapeutic or protective immunity in women with advanced stage breast cancer.

HER2/neu is a member of the epidermal growth factor receptor family and encodes a 185-kd tyrosine kinase receptor involved in regulating cell growth and proliferation. (Popescu N C, King C R, Kraus M H. Localization of the human erbB-2 gene on normal and rearranged chromosome 17 to bands q12-21.32. Genomics 1989; 4:362-366; Yarden Y, Sliwkowski M X. Untangling the ErbB signaling network. Nat Rev Mol Cell Bio 2001; 2:127-137.) Overexpression and/or amplification of HER2/neu is found in 25-30% of invasive breast cancers (BCa) and is associated with more aggressive tumors and a poorer clinical outcome. (Slamon D J, Clark G M, Wong S G, et al. Human breast cancer: correlation of relapse and survival with amplification of the HER-2/neu oncogene. Science 1987; 235:177-182; Slamon D J, Godolphin W, Jones L A, et al. Studies of the HER-2/neu proto-oncogene in human breast and ovarian cancer. Science 1989; 244:707-12; Toikkanen S, Helin H, Isola J, Joensuu H. Prognostic significance of HER-2 oncoprotein expression in breast cancer: A 30-year follow-up. J Clin Oncol 1992; 10:1044-1048.)

Determining HER2/neu status is performed predominately via two tests, immunohistochemistry (IHC) and fluorescence in situ hybridization (FISH). IHC detects overexpression of HER2/neu protein and is reported on a semi-quantitative scale of 0 to 3+(0=negative, 1+=low expression, 2+=intermediate, and 3+=over-expression). FISH on the other hand detects amplification (excess copies) of the HER2/neu gene and is expressed as a ratio of HER2/neu gene copies to chromosome 17 gene copies and interpreted as "over-expression" if FISH is ≥2.0 copies. (Hicks D G, Tubbs R R. Assessment of the HER2 status in breast cancer by fluorescence in situ hybridization: a technical review with interpretive guidelines. Hum Pathol 2005; 36:250-261.) Concurrence rate of IHC and FISH is approximately 90%. (Jacobs T W, Gown A M, Yaziji H, et al. Specificity of HercepTest in determining HER-2/neu status of breast cancers using the United States Food and Drug Administration-approved scoring system. J Clin Oncol 1999; 17:1533-1541.) FISH is considered the gold standard, as retrospective analysis reveals it is a better predictor of trastuzumab (Tz) response; it is more objective and reproducible. (Press M F, Slamon D J, Flom K J, et al. Evaluation of HER-2/neu Gene Amplification and Overexpression: Comparison of Frequently Used Assay Methods in a Molecularly Characterized Cohort of Breast Cancer Specimens. J Clin Oncol 2002; 14:3095-3105; Bartlett J, Mallon E, Cooke T. The clinical evaluation of HER-2 status: which test to use? J Pathol 2003; 199:411-417; Wolff A C, Hammond M E H, Schwartz J N, et al. American Society of Clinical Oncology/College of American Pathologists guideline recommendations for human epidermal growth factor receptor 2 testing in breast cancer. J Clin Oncol 2007; 25:118-145.)

Identification and quantification of HER2/neu as a proto-oncogene has led to humoral or antibody-based passive immunotherapy, to include the use of Tz (Herceptin®). Tz is a recombinant, humanized monoclonal antibody that binds the extracellular juxtamembrane domain of HER2/neu protein. (Plosker G L, Keam S J. Trastuzumab: A review of its use in the management of HER2-positive metastatic and early-stage breast cancer. Drugs 2006; 66:449-475.) Tz is indicated for HER2/neu over-expressing (IHC 3+ or FISH≥2.0) node-positive (NP) and metastatic BCa patients, (Vogel C L, Cobleigh M A, Tripathy D, et al. Efficacy and safety of trastuzumab as a single agent in first-line treatment of HER2-overexpressing metastatic breast cancer. J Clin Oncol 2002; 20:719-726; Piccart-Gebhart M J, Procter M, Leyland-Jones B, et al. Trastuzumab after adjuvant chemotherapy in HER2-positive breast cancer. N Engl J Med 2005; 353:1659-1672) and shows very limited activity in patients with low to intermediate HER2/neu expression. (Herceptin (Trastuzumab) prescription product insert. South San Francisco, Calif.: Genentech Inc; revised September 2000.)

Another form of immunotherapy being pursued is vaccination and active immunotherapy targeting a cellular immune response to epitopes on tumor associated antigens (TAA) such as HER2/neu. HER2/neu is a source of several immunogenic peptides that can stimulate the immune system to recognize and kill HER2/neu-expressing cancer cells. (Fisk B, Blevins T L, Wharton J T, et al. Identification of immunodominant peptide of the HER2/neu proto-oncogene recognized by ovarian tumor-specific CTL lines. J Exp Med 1995; 181:2109-2117.)

E75 (KIFGSLAFL, HER2/neu, 369-377) is a peptide sequence in the HER2/neu proto-oncogene family and is in use in clinical trials as an anti-cancer vaccine to stimulate cytotoxic T lymphocytes (CTL) to destroy cancer cells. (Zaks, T. et. al. Immunization with a peptide epitope (369-377) from HER-2/neu leads to peptide specific cytotoxic T lymphocytes that fail to recognize HER-2/neu+ tumors. Cancer Research. 58 (21): 4902-8. 1998; Knutson K L, Schiffman K, Cheever M A, et al: Immunization of cancer patients with HER-2/neu, HLA-A2 peptide, p 369-377, results in short-lived peptide-specific immunity. Clin Cancer Res 8:1014-1018, 2002; Murray J L, Gillogly M E, Przepiorka D, et al: Toxicity, immunogenicity, and induction of E75-specific tumorlytic CTLs by HER-2 peptide E74 (369-377) combined with granulocyte macrophage colony-stimulating factor in HLA-A2+ patients with metastatic breast and ovarian cancer. Clin Cancer Res 8:3407-3418, 2002; Avigan D, Vasir B, Gong J, et al. Fusion cell vaccination of patients with metastatic breast and renal cell cancer induces immunological responses. Clin Cancer Res 2004: 10:4699-4708; Disis M L, Gooley T A, Rinn K, et al. Generation of T-cell immunity to the HER2/neu protein after active immunization with HER2/neu peptide-based vaccines. J Clin Oncol 2002; 20:2624-32; Disis M L, Grabstein K H, Sleath P R, et al. Generation of immunity to the HER-2/neu oncogenic protein in patients with breast and ovarian cancer using a peptide-based vaccine. Clin Cancer Res 5:1289-1297, 1999.

Targeted passive immunotherapy based on the HER2/neu proto-oncogene has primarily revolved around the use of Tz (Herceptin®). Tz is a recombinant, humanized monoclonal antibody that binds the extracellular juxtamembrane domain of the HER2/neu protein. Tz is approved by regulatory authorities and indicated for treatment of HER2/neu overexpressing (IHC 3+ or FISH>2.0) tumors in metastatic breast cancer patients and in the adjuvant setting for node-positive breast cancer patients. Tz has undergone multiple clinical trials and is now routinely used in the treatment of metastatic patients and in the adjuvant treatment of high risk breast cancer patients with overexpression of HER2/neu. Tz, however, shows limited activity in patients with low to intermediate HER2/neu expression. Therefore, based on the previous results seen with Tz, immunogenic peptide vaccines targeting HER2/neu would not be expected to be effective in cancer patients with low and intermediate levels of HER2/neu tumor expression.

Thus, there is a need in the art to exploit the immunoprotective and therapeutic potential of E75 to produce vaccines that offer breast cancer patients in clinical remission reliable protection against recurrence of the disease.

SUMMARY

The invention features methods of inducing and maintaining immunity against breast cancer relapse in patients in breast cancer clinical remission. The methods comprise administering to the patient an effective amount of a composition comprising a pharmaceutically effective carrier and a peptide having the amino acid sequence SEQ ID NO:2. The administration can be accomplished by any means suitable in the art, such as inoculation or injection, and more particularly intradermal injection, which can occur with one or more separate doses. Such doses can comprise an equal concentration of the peptide and an immunoadjuvant, can be administered substantially concurrently, and can be administred at one inoculation site or spaced apart from each other on the surface of the skin. The composition can be administered approximately three to six times or more on a monthly basis until the protective immunity is established. In some aspects, the composition further comprises an adjuvant such as recombinant human granulocyte macrophage-colony stimulating factor (GM-CSF).

In some aspects, the methods further comprise administering to the subject a booster vaccine dose, which comprises an effective amount of a composition comprising a pharmaceutically effective carrier and a peptide having SEQ ID NO:2. In some aspects, the composition of the booster further comprises an adjuvant such as GM-CSF. The administration of a booster can be carried out by inoculation or injection, and can be can be administered every six or 12 months thereafter.

The patient can be any mammal, and is preferably a human. In certain aspects, the human is positive for major histocompatibility antigen blood-typed as human leukocyte antigen A2 or human leukocyte antigen A3. In other aspects, the human is positive for the expression of detectable levels of HER2/neu. In some aspects, the human is a low or intermediate HER2/neu-expressor. For example, in some preferred aspects, the human has a immunohistochemistry (IHC) rating of 1+ or 2+ and/or a fluorescence in situ hybridization (FISH) rating of less than 2.0. In other aspects, the human can have an IHC rating up to 3+. In other aspects, the human can be overexpressors of HER2/neu. For example, in some preferred aspects, the human has an immunohistochemistry (IHC) rating of 3+ and/or a fluorescence in situ hybridization (FISH) rating of greater than or equal to 2.0.

The invention also features compositions for use in the inventive methods. Such compositions comprise a pharmaceutically acceptable carrier, an effective amount of a peptide having the amino acid sequence SEQ ID NO:2, an adjuvant such as granulocyte macrophage-colony stimulating factor, and an optimized immunization schedule. In some specific aspects, the preferred concentrations and schedules of the vaccine composition include: (1) 1 mg/ml peptide and 0.25 mg/ml adjuvant, (2) 0.5 mg/ml peptide and 0.25 mg/ml adjuvant, (3) 0.1 mg/ml peptide and 0.25 mg/ml adjuvant, and (4) 0.5 mg/ml peptide and 0.125 mg/ml adjuvant, each with monthly inoculations for 6 consecutive months followed by annual booster inoculations for 3 or more years.

BRIEF DESCRIPTION OF THE DRAWINGS

The accompanying drawings, which are included to provide a further understanding of the invention and are incorporated in and constitute a part of this specification, illustrate aspects of the invention and together with the description serve to explain the principles of the invention. In the drawings.

A. In vitro immune response—all in vitro pre-max % specific CD8+ T-cells statistically increased (LE p<0.001, OE p<0.001) and LE patients had increased max response compared to OE patients (p=0.04).

B. In vivo immune response—all in vivo pre-post DTHs statistically increased (LE p<0.001, OE p=0.02).

C. Recurrence rates—recurrence rates were decreased in vaccinated LE and OE patients, albeit not statistically significant.

D. Mortality rates—vaccinated LE patients had a trend towards decreased mortality rates (p=0.08).

FIG. 12A to FIG. 12D show immunologic (mean±SE) and clinical responses (absolute recurrence and mortality rates) of patients enrolled in E75 Phase II trial by HER2/neu IHC expression level (0, 1+, 2+, 3+).

A. In vitro immune response—all in vitro pre-max % specific CD8+ T-cells statistically increased, whereas only HER2/neu 1+ pre-long term trended towards significance (p=0.08).

B. In vivo immune response—all in vivo pre-post DTHs statistically increased (0 p=0.03, 1+p=0.02, 2+p=0.02, 3+p=0.05).

C. Recurrence rates—recurrence rates were decreased in all vaccinated IHC levels, albeit not statistically significant.

D. Mortality rates—mortality rates decreased in all vaccinated IHC levels and was statistically significant in HER2/neu IHC 1+ vaccine patients (p=0.04).

Figure 13A:
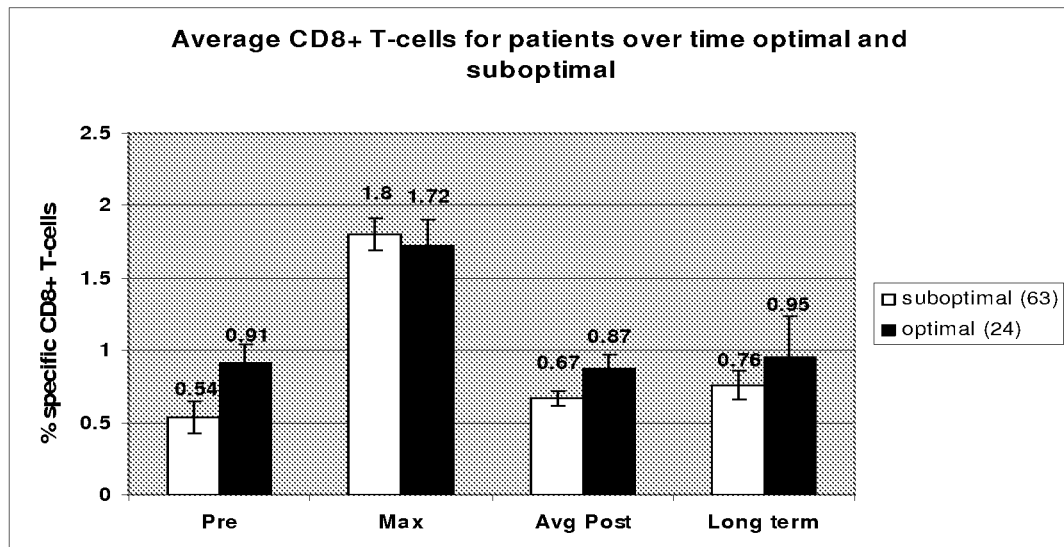
Figure 13B:
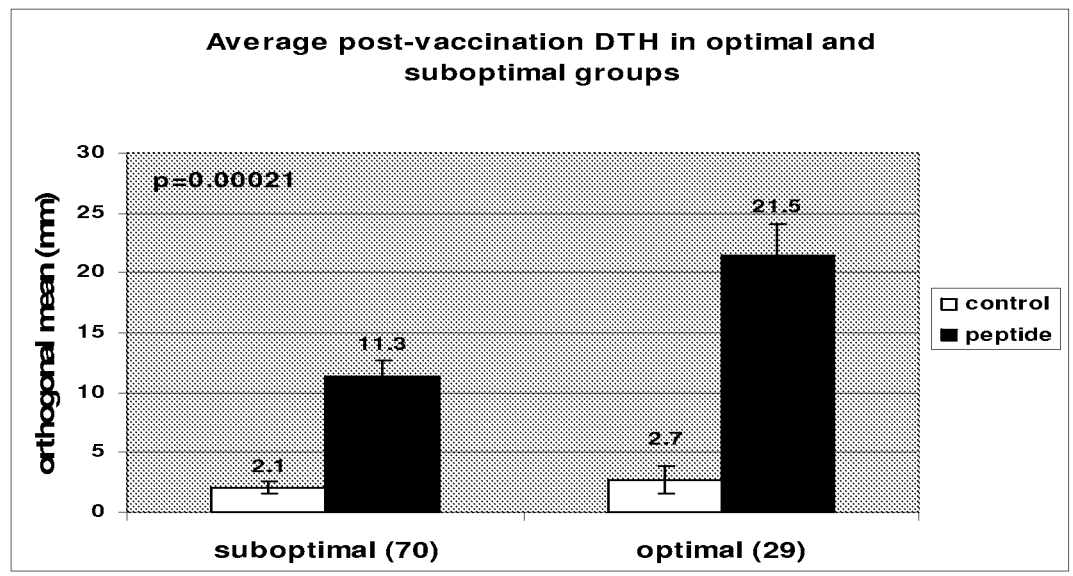

FIGS. 13A and 13B show Dimer Assay and DTH per ODG vs. SDG. (A) A significant difference in the ODG vs. SDG was seen in the average pre-vaccine CD8+E75-specific T cells levels (0.91+0.13% vs. 0.54+0.11%, p=0.03). No significant difference seen between the average maximum CD8+E75-specific T cell levels. The optimal dose showed a trend toward an increase in the average of monthly post vaccination percent of CD8+E75-specific T cells (0.87+0.10% vs. 0.67+0.05%, p=0.07). No difference seen in the average long term CD8+E75-specific T cell levels between groups at 6 months. (B) Orthogonal mean DTH response (mm) between the ODG vs. SDG showed no difference to the control inoculum (3.0+1.1 mm vs. 2.0+0.5 mm). DTH response to the peptide was significantly elevated in the ODG vs. the SDG (21.5+2.5 mm vs. 11.3+1.3 mm, p=0.00021).

Figure 14:
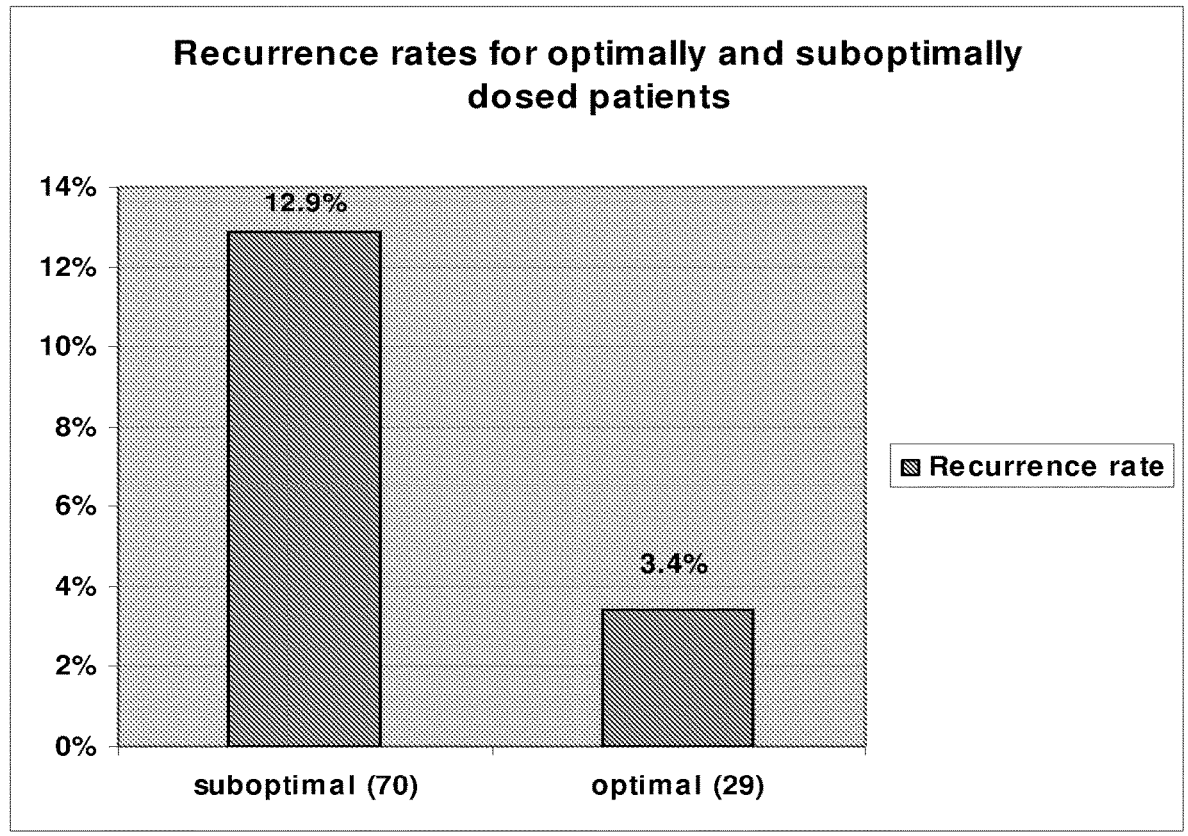

FIG. 14 shows comparison of the clinical recurrence rates between the SDG and ODG. Compared to the SDG, the ODG demonstrated a trend toward lower recurrence rates (p=0.27) but at a significantly shorter median follow-up. However, the ODG consisted of younger patients with significantly more aggressive disease.

DETAILED DESCRIPTION

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The term "prevent" refers to any success or indicia of success in the forestalling of breast cancer recurrence/relapse in patients in clinical remission, as measured by any objective or subjective parameter, including the results of a radiological or physical examination.

"Effective amount" or "therapeutically effective amount" are used interchangeably herein, and refer to an amount of a compound, material, or composition, as described herein effective to achieve a particular biological result such as, but not limited to, biological results disclosed, described, or exemplified herein. Such results can include, but are not limited to, the prevention of breast cancer, and more particularly, the prevention of recurrent breast cancer, e.g., the prevention of relapse in a subject, as determined by any means suitable in the art. Optimal therapeutic amount refers to the dose, schedule and the use of boosters to achieve the best therapeutic outcome.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

"Protective immunity" or "protective immune response," means that the subject mounts an active immune response to an immunogenic component of an antigen such as the breast cancer antigens described and exemplified herein, such that upon subsequent exposure to the antigen, the subject's immune system is able to target and destroy cells expressing the antigen, thereby decreasing the incidence of morbidity and mortality from recurrence of cancer in the subject. Protective immunity in the context of the present invention is preferably, but not exclusively, conferred by T lymphocytes.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Peptide" refers to any peptide comprising two or more amino acids joined to each other by peptide bonds or modified peptide bonds, i.e., peptide isosteres. Polypeptide refers to both short chains, commonly referred to as peptides, oligopeptides or oligomers, and to longer chains, generally referred to as proteins. Polypeptides can contain amino acids other than the 20 gene-encoded amino acids. Polypeptides include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification can be present in the same or varying degrees at several sites in a given polypeptide. Also, a given polypeptide can contain many types of modifications. Polypeptides can be branched as a result of ubiquitination, and they can be cyclic, with or without branching. Cyclic, branched and branched cyclic polypeptides can result from natural post-translational processes or can be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

"Booster" refers to a dose of an immunogen administered to a patient to enhance, prolong, or maintain protective immunity and to overcome the down-regulation of T-cell responses mediated by regulatory T-cells.

"Free of breast cancer" or "disease free" or NED (No Evidence of Disease) means that the patient is in clinical remission induced by treatment with the current standard of care therapies. By "remission" or "clinical remission," which are used synonymously, it is meant that the clinical signs, radiological signs, and symptoms of breast cancer have been significantly diminished or have disappeared entirely based on clinical diagnostics, although cancerous cells can still exist in the body. Thus, it is contemplated that remission encompasses partial and complete remission. The presence of residual cancer cells can be enumerated by assays such as CTC (Circulating Tumor Cells) and can be predictive of recurrence.

"Relapse" or "recurrence" or "resurgence" are used interchangeably herein, and refer to the radiographic diagnosis of return, or signs and symptoms of return of breast cancer after a period of improvement or remission.

Breast cancer is a major health concern for women worldwide. Breast cancer vaccines that have been attempted to date have been limited in efficacy, particularly with respect to preventing relapse in disease-free patients. In accordance with the present invention, it has been determined that recurrence of breast cancer in disease-free patients can be effectively prevented by administration to the patient of a peptide of the HER2/neu oncogene, E75 (SEQ ID NO:2) under certain conditions. It has also been unexpectedly determined that the E75 peptide is associated with MHC HLA-A2 and -A3, and thus can induce protective immunity in patients having the HLA-A2 and -A3 haplotype.

Accordingly, the present invention features vaccine compositions for inducing protective immunity against breast cancer relapse. The invention also features methods for inducing and for maintaining protective immunity against breast cancer, and more particularly against recurrent breast cancer. In some aspects, the methods comprise administering to a subject an effective amount of a composition comprising a pharmaceutically effective carrier and a polypeptide having the amino acid sequence SEQ ID NO:2. Variants of SEQ ID NO:2, including those with modified side chains of amino acids as described by U.S. Pat. Publ. No. 20050169934 are suitable for use as an immunogen in the inventive vaccine compositions and methods.

The subject can be any animal, and preferably is a mammal such as a human, mouse, rat, hamster, guinea pig, rabbit, cat, dog, monkey, cow, horse, pig, and the like. Humans are most preferred. In highly preferred aspects, the humans are positive for the HLA-A2 or HLA-A3 haplotypes. In other preferred aspects, the humans are positive for the expression of human HER2/neu, including preferentially humans with low and/or intermediate HER2/neu expressing tumors, as well as humans that are overexpressors of HER2/neu.

The vaccine compositions can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form.

The vaccine compositions can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine compositions are preferably formulated for inoculation or injection into the subject. For injection, the vaccine compositions of the invention can be formulated in aqueous solutions such as water or alcohol, or in physiologically compatible buffers such as Hanks's solution, Ringer's solution, or physiological saline buffer. The solution can contain formulatory agents such as suspending, preserving, stabilizing and/or dispersing agents. Injection formulations can also be prepared as solid form preparations which are intended to be converted, shortly before use, to liquid form preparations suitable for injection, for example, by constitution with a suitable vehicle, such as sterile water, saline solution, or alcohol, before use.

The vaccine compositions can also be formulated in sustained release vehicles or depot preparations. Such long acting formulations can be administered by inoculation or implantation (for example subcutaneously or intramuscularly) or by injection. Thus, for example, the vaccine compositions can be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers.

The vaccine compositions can comprise agents that enhance the protective efficacy of the vaccine, such as adjuvants. Adjuvants include any compound or compounds that act to increase a protective immune response to the E75 peptide antigen, thereby reducing the quantity of antigen necessary in the vaccine, and/or the frequency of administration necessary to generate a protective immune response. Adjuvants can include for example, emulsifiers, muramyl dipeptides, avridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), Mycobacterialphlei (*M. phlei*) cell wall extract (MCWE) (U.S. Pat. No. 4,744,984), *M. phlei* DNA (M-DNA), and M-DNA-*M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emuslsions; however, FCA also contains a killed *Mycobacterium* sp.

Immunomodulatory cytokines can also be used in the vaccine compositions to enhance vaccine efficacy, for example, as an adjuvant. Non-limiting examples of such cytokines include interferon alpha (IFN-α), interleukin-2 (IL-2), and granulocyte macrophage-colony stimulating factor (GM-CSF), or combinations thereof. GM-CSF is highly preferred.

Vaccine compositions comprising E75 peptide antigens and further comprising adjuvants can be prepared using techniques well known to those skilled in the art including, but not limited to, mixing, sonication and microfluidation. The adjuvant can comprise from about 10% to about 50% (v/v) of the vaccine composition, more preferably about 20% to about 40% (v/v), and more preferably about 20% to about 30% (v/v), or any integer within these ranges. About 25% (v/v) is highly preferred.

Administration of the vaccine compositions can be by infusion or injection (e.g., intravenously, intramuscularly, intracutaneously, subcutaneously, intrathecal, intraduodenally, intraperitoneally, and the like). The vaccine compositions can also be administered intranasally, vaginally, rectally, orally, or transdermally. Additionally, vaccine compositions can be administered by "needle-free" delivery systems. Preferably, the compositions are administered by intradermal injection. Administration can be at the direction of a physician or physician assistant.

The injections can be split into multiple injections, with such split inoculations administered preferably substantially concurrently. When administered as a split inoculation, the dose of the immunogen is preferably, but not necessarily, proportioned equally in each separate injection. If an adjuvant is present in the vaccine composition, the dose of the adjuvant is preferably, but not necessarily, proportioned equally in each separate injection. The separate injections for the split inoculation are preferably administered substantially proximal to each other on the patient's body. In some preferred aspects, the injections are administered at least about 1 cm apart from each other on the body. In some preferred aspects, the injections are administered at least about 2.5 cm apart from each other on the body. In highly preferred aspects, the injections are administered at least about 5 cm apart from each other on the body. In some aspects, the injections are administered at least about 10 cm apart from each other on the body. In some aspects, the injections are administered more than 10 cm apart from each other on the body, for example, at least about 12.5. 15, 17.5, 20, or more cm apart from each other on the body. Primary immunization injections and booster injections can be administered as a split inoculation as described and exemplified herein.

Various alternative pharmaceutical delivery systems can be employed. Non-limiting examples of such systems include liposomes and emulsions. Certain organic solvents such as dimethylsulfoxide also can be employed. Additionally, the vaccine compositions can be delivered using a sustained-release system, such as semipermeable matrices of solid polymers containing the therapeutic agent. The various sustained-release materials available are well known by those skilled in the art. Sustained-release capsules can, depending on their chemical nature, release the vaccine compositions over a range of several days to several weeks to several months.

To prevent breast cancer recurrence in a patient who is in breast cancer remission, a therapeutically effective amount of the vaccine composition is administered to the subject. A therapeutically effective amount will provide a clinically significant increase in the number of E75-specific cytotoxic T-lymphocytes (CD8$^+$) in the patient, as well as a clinically significant increase in the cytotoxic T-lymphocyte response to the antigen, as measured by any means suitable in the art. In the patient on the whole, a therapeutically effective amount of the vaccine composition will destroy residual microscopic disease and significantly reduce or eliminate the risk of recurrence of breast cancer in the patient.

The effective amount of the vaccine composition can be dependent on any number of variables, including without limitation, the species, breed, size, height, weight, age, overall health of the patient, the type of formulation, the mode or manner or administration, or the presence or absence of risk factors that significantly increase the likelihood that the breast cancer will recur in the patient. Such risk factors include, but are not limited to the type of surgery, status of lymph nodes and the number positive, the size of the tumor, the histologic grade of the tumor, the presence/absence of hormone receptors (estrogen and progesterone receptors), HER2/neu expression, lymphovascular invasion, and genetic predisposition (BRCA 1 and 2). In some preferred aspects, the effective amount is dependent on whether the patient is lymph node positive of lymph node negative, and if the patient is lymph node positive, the number and extent of the positive nodes. In all cases, the appropriate effective amount can be routinely determined by those of skill in the art using routine optimization techniques and the skilled and informed judgment of the practitioner and other factors evident to those skilled in the art. Preferably, a therapeutically effective dose of the vaccine compositions described herein will provide the therapeutic preventive benefit without causing substantial toxicity to the subject.

Toxicity and therapeutic efficacy of the vaccine compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Vaccine compositions that exhibit large therapeutic indices are preferred. Data obtained from cell culture assays and animal studies can be used in formulating a range of dosage for use in patients. The dosage of such vaccine compositions lies preferably within a range of circulating concentrations that include the ED50 with little or no toxicity. The dosage can vary within this range depending upon the dosage form employed and the route of administration utilized.

Toxicity information can be used to more accurately determine useful doses in a specified subject such as a human. The treating physician can terminate, interrupt, or adjust administration due to toxicity, or to organ dysfunctions, and can adjust treatment as necessary if the clinical response is not adequate, to improve the response. The magnitude of an administered dose in the prevention of recurrent breast cancer will vary with the severity of the patient's condition, relative risk for recurrence, or the route of administration, among other factors. The severity of the patient's condition can, for example, be evaluated, in part, by standard prognostic evaluation methods.

The vaccine compositions can be administered to a patient on any schedule appropriate to induce and/or sustain protective immunity against breast cancer relapse, and more specifically to induce and/or sustain a cytotoxic T lymphocyte response to E75 (SEQ ID NO:2). For example, patients can be administered a vaccine composition as a primary immunization as described and exemplified herein, followed by administration of a booster to bolster and/or maintain the protective immunity.

In some aspects, patients can be administered the vaccine compositions 1, 2 or more times per month. Once per month for six consecutive months is preferred to establish the protective immune response, particularly with respect to the primary immunization schedule. In some aspects, boosters can be administered at regular intervals such as every 6 or more months after completion of the primary immunization schedule. Administration of the booster is preferably every 6 months. Boosters can also be administered on an as-needed basis.

The vaccine administration schedule, including primary immunization and booster administration, can continue as long as needed for the patient, for example, over the course of several years, to over the lifetime of the patient. In some aspects, the vaccine schedule includes more frequent administration at the beginning of the vaccine regimen, and includes less frequent administration (e.g., boosters) over time to maintain the protective immunity.

The vaccine can be administered at lower doses at the beginning of the vaccine regimen, with higher doses administered over time. The vaccines can also be administered at higher doses at the beginning of the vaccine regimen, with lower doses administered over time. The frequency of primary vaccine and booster administration and dose of E75 administered can be tailored and/or adjusted to meet the particular needs of individual patients, as determined by the administering physician according to any means suitable in the art.

In some aspects, the vaccine compositions, including compositions for administration as a booster, comprise from about 0.1 mg to about 10 mg of E75 peptide. In some preferred aspects, the compositions comprise about 0.5 mg of E75. In some preferred aspects, the compositions comprise about 2 mg of E75. In some preferred aspects, the compositions comprise about 1 mg of E75.

In some preferred aspects, the vaccine compositions comprising E75, including compositions for administration as a booster, further comprise GM-CSF. Such compositions preferably comprise from about 0.01 mg to about 0.5 mg of GM-CSF. In some preferred aspects, the compositions comprise about 0.125 mg of GM-CSF. In some preferred aspects, the compositions comprise about 0.25 mg of GM-CSF.

In some particularly preferred aspects, the vaccine compositions comprise 1 mg of E75 peptide and from 0.125 to 0.250 mg of GM-CSF in a total volume of 1 ml, and are administered monthly as a split inoculation of 0.5 ml each, administered by injections about 5 cm apart on the patient's body, and administered concurrently or admixed. The administration schedule is preferably monthly for six months. After a period of about 48 hours, the injection site can be assessed for local reaction of erythema and induration. If the reactions at both sites are confluent and the area of total induration measures >100 mm (or the patient experiences any >grade 2 systemic toxicity), then the dose of GM-CSF can be reduced, for example, by half, though it is intended that the peptide dose remain the same. If the patient presents a robust reaction on subsequent doses, then further reduction of GM-CSF can occur, for example, reducing by half. If the patient does not present with a robust reaction, then the patient can continue with the higher GM-CSF dose. In some aspects, the administration schedule and dosing of the booster is similarly determined, with boosters beginning with administration of vaccine compositions comprising 1 mg of E75 and 0.25 mg GM-CSF, administered about every six months following the conclusion of the primary immunization vaccine schedule.

The following Exemplary Aspects of specific examples for carrying out the present invention are offered for illustrative purposes only, and are not intended to limit the scope of the present invention in any way.

Example 1

Patient Selection

The node-positive (NP) and node-negative (NN) trials were approved by the local Institutional Review Boards and conducted at Walter Reed Army Medical Center, Washington, D.C. and the Joyce Murtha Breast Care Center, Windber, Pa. under an investigational new drug application (BB-IND #9187). All patients had histologically confirmed breast cancer (BCa), and completed a standard course of surgery, chemotherapy, and radiation therapy (as required) before enrollment. Patients on hormonal therapy were continued on their specific regimen. After proper counseling and consenting, BCa patients were enrolled to the appropriate trial (NP or NN) and then HLA typed, since E75 binds primarily HLA-A2 found in approximately 40-50% of the general population. HLA-A2+ patients were vaccinated, and HLA-A2− patients were observed prospectively for clinical recurrence. HLA-A3+ patients were enrolled into a parallel trial with the A2 patients, and treated on the active dose schedule at the time of enrollment. Before vaccination, patients were skin tested with a panel of recall antigens (mumps, tetanus, and *Candida*). Patients were considered immunocompetent if they reacted (>5 mm) to >2 antigens.

A total of 186 patients were enrolled in both E75 vaccine trials (NP=95, NN=91), who were disease-free after standard therapy, but at high risk for recurrence. After HLA-A2+, and later HLA-A3+, patients (n=101) were vaccinated (49 NP and 52 NN; 90 HLA-A2+ and 11 HLA-A3+). All other patients (n=85) were assigned to observation. Five vaccine and four observation patients withdrew from the study, though none due to toxicity. Therefore, 96 vaccinated patients and 81 observation patients were available for analysis. Demographics and prognostic factors for both groups are presented in Table 1.

TABLE 1

Demographic and prognostic factors for vaccinated and observation patients.

|  | Vaccinated, HLA-A2+, A3+ (n = 96)† | Observed, HLA-A2−, A3− (n = 81)‡ | P |
|---|---|---|---|
| Median age, years | 58.9 | 55.1 |  |
| Range, years | 32-80 | 34-87 | 0.33 |
| Race |  |  |  |
| White, % | 89.6 | 81.5 |  |
| Other, % | 10.4 | 18.5 | 0.12 |

TABLE 1-continued

Demographic and prognostic factors for vaccinated and observation patients.

|  | Vaccinated, HLA-A2+, A3+ (n = 96)† | Observed, HLA-A2−, A3− (n = 81)‡ | P |
|---|---|---|---|
| Tumor size |  |  |  |
| T1, % | 69.8 | 60.5 | 0.20 |
| T2-T4, % | 30.2 | 39.5 | 0.20 |
| Histological grade |  |  |  |
| I-II, % | 64.5 | 59.5 | 0.50 |
| III, % | 35.5 | 40.5 | 0.50 |
| Node-positive, % | 46.9 | 56.8 | 0.19 |
| Median + nodes (NP only) | 2.0 | 2.5 |  |
| Range | 1-25 | 1-15 | 0.17 |
| HER2/neu IHC 3+ or FISH +, % | 25.8 | 28.4 | 0.32 |
| Hormone receptor negative, % | 31.6 | 17.3 | 0.03 |
| XRT, % | 71.9 | 80.2 | 0.20 |
| Chemoprevention, % | 65.6 | 78.8 | 0.05 |
| Adjuvant Herceptin, % | 5.2 | 3.7 | 0.60 |

†101 patients enrolled to vaccine arm, 2 switched to observation, 1 withdrew for adjuvant trastuzumab, 1 due to an extended unrelated illness, and 1 patient for personal reasons.
‡85 patients enrolled to observation arm, 2 lost to follow-up and 4 withdrew for our MHC II peptide vaccine trial. Two patients were gained from the vaccine arm.

The two groups were equivalent in most standard prognostic categories. However, more vaccinated patients were hormone-receptor negative, and, therefore, fewer patients in the vaccine group were on adjuvant hormonal therapy. In looking at the individual trials, more vaccinated patients in the NN trial compared to controls had HER2/neu overexpressing tumors (25.0% vs. 7.1%, P<0.05), and fewer received adjuvant radiotherapy (64.7% vs. 85.7%, P<0.05).

During the trials, it was determined that E75 could be used in HLA-A3+ patients based on binding affinity data obtained from two commonly used HLA-peptide binding algorithms: BIMAS (SEQ ID NO:3) and SYFPEITHI (SEQ ID NO:4). Additionally, pre-clinical evaluation demonstrated that E75-stimulated HLA-A3+ CTL could lyse HLA-A3+ HER2/neu-expressing cancer cells (not shown).

Although there was no difference in the nodal status of the HLA-A3 subset compared to the HLA-A2 subset (54.5% vs. 45.9%, P=0.59), they tended to have smaller tumors (90.9% T1 vs. 65.7%, P=0.08), were less likely to have hormonally insensitive tumors (18.2% vs. 29.6%, P=0.4), and had less HER2/neu overexpressing tumors (0% vs. 31.5%, P=0.028).

Example 2

Vaccination and Clinical Protocol

The E75 peptide was commercially produced in good manufacturing practices grade by NeoMPS, Inc. (San Diego, Calif.). Peptide purity (>95%) was verified by high-performance liquid chromatography and mass spectrometry, and the amino acid content was determined by amino acid analysis. Sterility and general safety testing was carried out by the manufacturer. Lyophilized peptide was reconstituted in sterile saline at 100 µg, 500 µg, or 1000 µg in 0.5 ml. At the time of administration, the peptide was thawed and mixed with GM-CSF (Berlex, Seattle, Wash.) in 0.5 ml, and the 1.0 ml inoculation was split and given intradermally at two sites 5 cm apart. All inoculations were given in the same extremity.

Vaccination Series.

The NP trial was designed as a two stage safety trial with escalating doses of peptide in the initial stage and alterations of schedule in the latter stage. Details of the vaccine series have been previously published (Peoples G E et al. (2005)

J. Clin. Oncol. 23:7536-45). Briefly, 3-6 patients (HLA-A2+ or HLA-A3+) were each assigned to receive four or six monthly injections of 100 µg, 500 µg, or 1000 µg of E75 (100.6, 500.4, 500.6, 1000.4 and 1000.6, respectively) (Table 2). Groups were ultimately expanded in order to determine and confirm optimal dosing in NP patients, accounting for the larger number of patients in the latter dose groups.

TABLE 2

NP and NN trial designs.

| Patient Group | No. of patients HLA-A2+ (A3+) | Peptide dose† (µg) | GM-CSF dose (µg) | Months vaccinated‡ |
|---|---|---|---|---|
| Node-positive | | | | |
| 100.6 | 2* | 100 | 250 | 0, 1, 2, 3, 4, 5 |
| 500.4 | 6 | 500 | 250 | 0, 1, 2, 5 |
| 500.6 | 6 | 500 | 250 | 0, 1, 2, 3, 4, 5 |
| 1000.4 | 9 (2) | 1000 | 250 | 0, 1, 2, 5 |
| 1000.6 | 16 (4) | 1000 | 250 | 0, 1, 2, 3, 4, 5 |
| Node-negative | | | | |
| 500.125.3 | 10 | 500 | 125 | 0, 1, 5 |
| 500.125.4 | 10 | 500 | 125 | 0, 1, 2, 5 |
| 500.250.4 | 10 (3) | 500 | 250 | 0, 1, 2, 5 |
| 500.250.6 | 10 (2) | 1000 | 250 | 0, 1, 2, 3, 4, 5 |
| 1000.250.6 | 6 | 1000 | 250 | 0, 1, 2, 3, 4, 5 |
| Total | 85 (11) | | | |

†Peptide was suspended in 0.5 ml sterile saline and combined with GM-CSF and sterile saline to final volume of 1.0 ml per inoculation.
‡Vaccines were administered every 3-4 weeks.
*One patient assigned to 100.6 group withdrew and no replacement at that dose group was designated.

The NN trial was designed to further delineate optimal biologic dosing by varying the dose of GM-CSF and altering the inoculation schedule. Patients with non-HER2/neu-expressing tumors were allowed in this trial to determine the feasibility of vaccinating a presumably antigen-naïve host. Ten patients were assigned to each dose group to receive three, four, or six monthly injections over five months (Table 2).

Peripheral Blood Mononuclear Cell (PBMC) Isolation and Cultures.

Blood was drawn before each vaccination and at one (post-vaccine) and six months (long-term) after vaccine series completion. 50 ml of blood was drawn and PBMCs were isolated. PBMCs were washed and re-suspended in culture medium and used as a source of lymphocytes.

Toxicity.

Patients were observed one hour post-vaccination for immediate hypersensitivity and returned 48-72 hours later to have their injection sites measured and questioned about toxicities. Toxicities were graded by the NCI Common Terminology Criteria for Adverse Events, v3.0 and reported on a scale from 0-5. Progression from one dose group to the next occurred only if no significant toxicity occurred in the lower dose group. Patient-specific results were reported based on maximal local and systemic toxicity occurring during the series.

Figure 1:
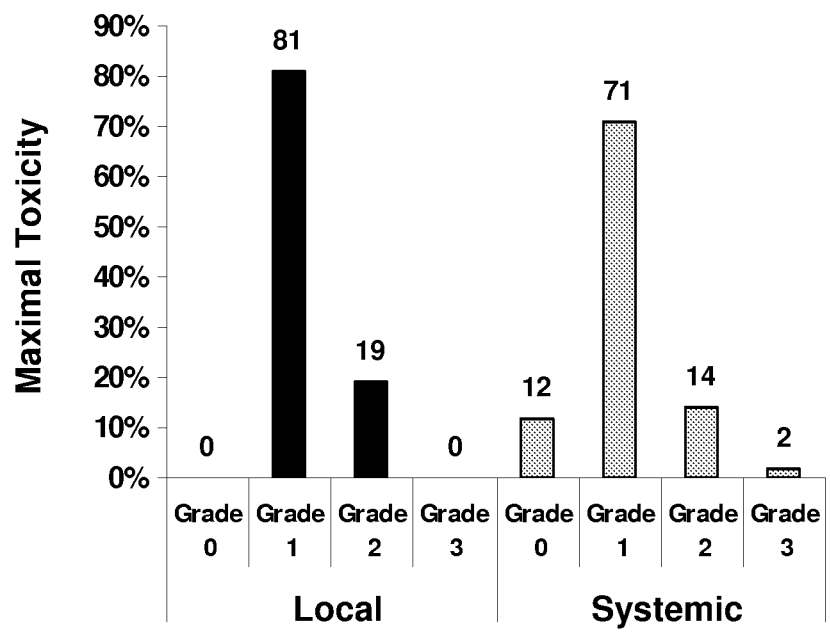
FIG. 1 shows the maximum local and systemic toxicity experienced by patients vaccinated with E75. Local toxicity (erythema and induration at injection site) is a desired effect showing a response to the vaccine. The most common grade 2 local toxicities were pruritis or discomfort requiring medication. Most common systemic toxicities were bone pain, flu-like symptoms and fatigue (commonly associated with GM-CSF) and lasted <24 hours. The two grade 3 systemic toxicities were angioedema of the tongue (after sixth inoculation) and bony pain.

Local and systemic toxicities were mild, and all patients completed the vaccine series. Local toxicities were grade 1 (81%) and grade 2 (19%). Systemic toxicity was minimal: grade 0 (12%), grade 1 (71%), grade 2 (14%) and grade 3 (2%) (FIG. 1) with no grade 4 or 5 systemic toxicities observed. Since toxicities observed are consistent with GM-CSF, a 50% dose reduction in GM-CSF was instituted in the event of significant local or systemic reactions (18.7% of patients).

Toxicity profiles were the same in A3 patients as their A2 counterparts: maximum local toxicity grade 1 (82%) and grade 2 (18%) for both groups. Maximum systemic toxicity (A3 vs. A2): grade 0 (0% vs. 15%), grade 1 (92% vs. 68%), grade 2 (8% vs. 14%) and grade 3 (0% vs. 2%; p=0.4). Local responses of A3 patients were identical to the A2 patients within the respective dose groups. Thus, there was no difference in the toxicity profile among the HLA-A3+ patients compared to the HLA-A2+ patients, and the local reactions were just as robust. Grade 2 local toxicity was 20% compared to 18%, respectively, suggesting similar in vivo immunogenicity.

Clinical Recurrences.

All patients were observed for clinical recurrence per standard of care cancer screening as dictated by the patient's primary oncologist. A patient was considered recurrent if biopsy proven or if treated for recurrence by the primary oncology team.

Figure 2:
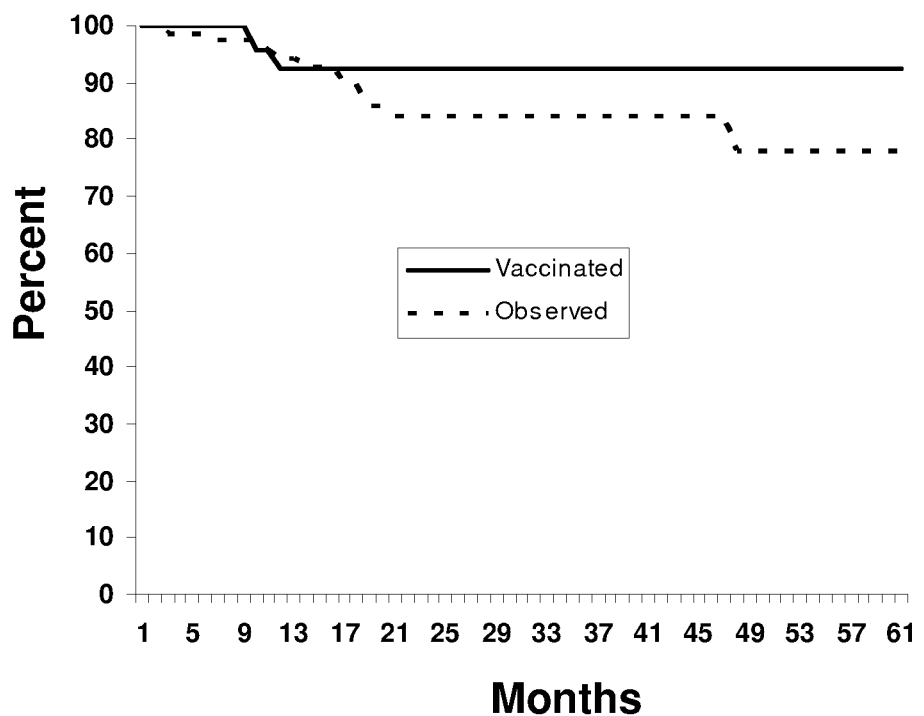
FIG. 2 shows Kaplan Meier disease-free survival curves at 20 months median follow-up. For 171 enrolled patients, the recurrence rate in the vaccinated group was 5.6% compared to 14.2% in the observation group (P=0.04) at a median follow-up of 20 months. The disease-free survival rates in the vaccinated and control groups were 92.5% and 77%, respectively.

Per protocol design, primary analysis was initiated at 18 months median follow-up. At completion of this analysis, 171 patients had been enrolled, and the recurrence rate in the vaccinated group was 5.6% compared to 14.2% in the observation group (P=0.04) at a median follow-up of 20 months. The disease-free survival rates in the vaccinated and control groups were 92.5% and 77%, respectively (FIG. 2). There were four deaths in the observation group (overall survival [OS] 95.1%) compared to only one death in the vaccinated group (OS 99%, P=0.1).

The follow-up of both trials was extended to five years despite waning immunity and lack of a booster inoculation in the protocol design. An updated analysis documented additional recurrences in both groups including a late recurrence in the vaccine group at 58 months. At a median follow-up of 26 months, there were 186 patients enrolled, and the recurrence rate was 8.3% in the vaccine group compared to 14.8% in the observation group (P=0.15). There was a different distribution of recurrences among these patients. Bone only recurrence accounted for 50% of the recurrences in the control patients (6/12) and 0% of the vaccinated recurrent patients (P=0.04).

Among the HLA A3+ patients, the recurrence rate was similar to the HLA-A2+ patients (9.1% vs. 8.2%).

Statistical Analysis.

Recurrence rates were compared between groups using survival analysis by the Kaplan-Meier method, and the proportion of subjects who had recurrences compared using log-ranked analysis. P values for clinico-pathologic factors were calculated using Wilcoxon, Fisher's exact test or $\chi^2$ as appropriate. P values for comparing pre-vaccination and post-vaccination dimer levels were calculated using Wilcoxon and for DTH using Student's t-test.

Example 3

HLA-A2:Immunoglobulin Dimer Assay

The presence of CD8+ E75-specific cells in freshly isolated PBMC from patients was directly assessed by using a dimer assay. In brief, the HLA-A2:immunoglobulin (Ig) dimer (PharMingen, San Diego, Calif.) was loaded with the E75 or control peptide (E37, folate binding protein (25-33) RIAWARTEL (SEQ ID NO:5)) by incubating 2 µg of dimer with an excess (5 µg) of peptide and 0.5 µg of β2-microglobulin (Sigma, St. Louis, Mo.) at 37° C. overnight then stored at 4° C. until used. PBMC were washed and re-suspended in PharMingen Stain Buffer (PharMingen) and added at 5×10⁵ cells/100 μl/tube in 5 ml round-bottom polystyrene tubes (Becton Dickinson, Mountain View, Calif.) and stained with the loaded dimers and antibodies. In each patient the level of CD8⁺ E75-specific cells was determined in response to each successive vaccination and all post-inoculation measurements were averaged for each patient and compared with their pre-inoculation levels.

E75-specific CTL were assessed in fresh ex vivo PMBCs by the dimer assay before each vaccination and at one (post-vaccination) and six months (long-term). The dimer assay has been previously shown to correlate with functional immune assays (cytotoxicity and cytokine secretion) (Peoples G E et al. (2005) J. Clin. Oncol. 23:7536-45). A pattern of increasing CD8⁺ E75-specific CTL was observed during the vaccine series, peaking and then receding to a plateau by completion.

Figure 3A:
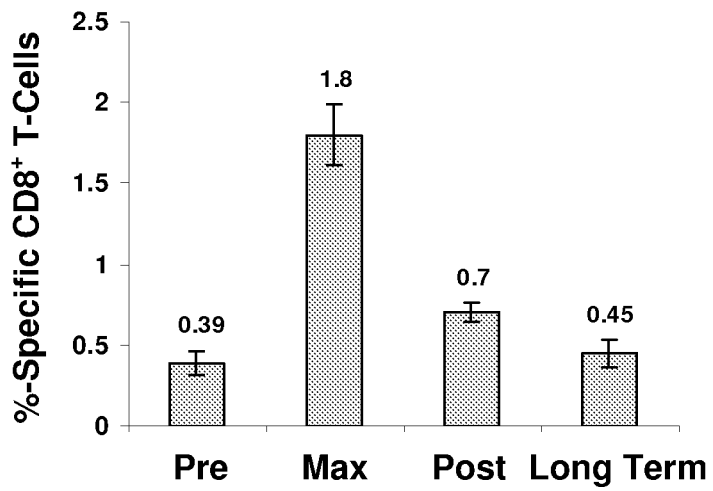
FIGS. 3A and 3B show the vaccine-induced E75 CTL response. (A) Vaccine-induced E75-specific CTL for all patients. The median levels of CD8+E75-specific CTL were significantly increased from pre-vaccination levels (0.39%, range 0-3.28%) to a maximum level (1.8, range 0.4-12.2%, P<0.0001), and post-vaccination level (0.70%, range 0.06-2.91%, P=0.002). There was no difference between pre-vaccine levels and long-term (six month) levels of specific CD8+ T-cells. (B) Vaccine-induced E75-specific CTL based on pre-existing immunity. Patients with and without pre-existing immunity showed identical patterns in response to E75 vaccination with similar median maximum and post-vaccination levels achieved for both. However, in those patients without pre-existing immunity, there was a significant increase in dimer levels from pre-vaccine to six months post-vaccine (0.13% [range 0-0.28%] vs. 0.45% [0-2.68%], P<0.0001).

The cumulative dimer responses for all patients are shown in FIG. 3A. There was a statistically significant increase in the median CD8⁺ E75-specific cells from pre-vaccine to post-vaccination and to peak levels. Long-term levels were not different from the pre-vaccination levels. Only 48.3% of patients maintained significant residual immunity (defined as dimer >0.5) six months post-vaccination.

Figure 3B:
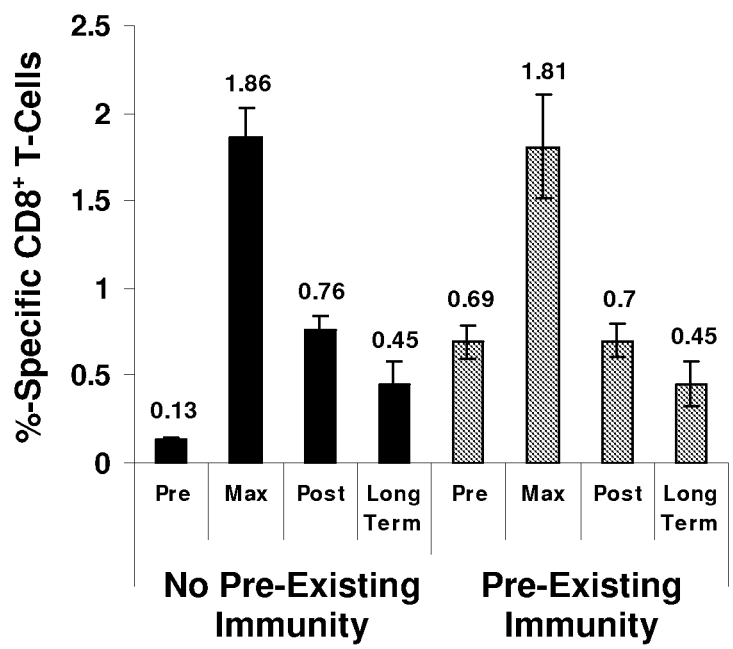

Pre-existing immunity to E75 (defined as dimer >0.3) was found in 42.7% of patients (FIG. 3B). The same pattern of dimer response was seen regardless of initial dimer levels. However, patients who lacked pre-existing immunity had a significant increase in their long-term dimer levels.

Example 4

Delayed Type Hypersensitivity

In both trials, a DTH reaction was assessed with 100 μg of E75 in 0.5 ml of normal saline (without GM-CSF) and 0.5 ml normal saline as a volume control one month after completion of the vaccine series as described previously (Peoples G E et al. (2005) J. Clin. Oncol. 23:7536-45). The DTH reaction was measured in two dimensions at 48-72 hours by using the sensitive ballpoint-pen method and reported as the orthogonal mean and compared to control. In the NN trial, a DTH was also performed pre-vaccination.

In Vivo Immune Response.

Figure 4A:
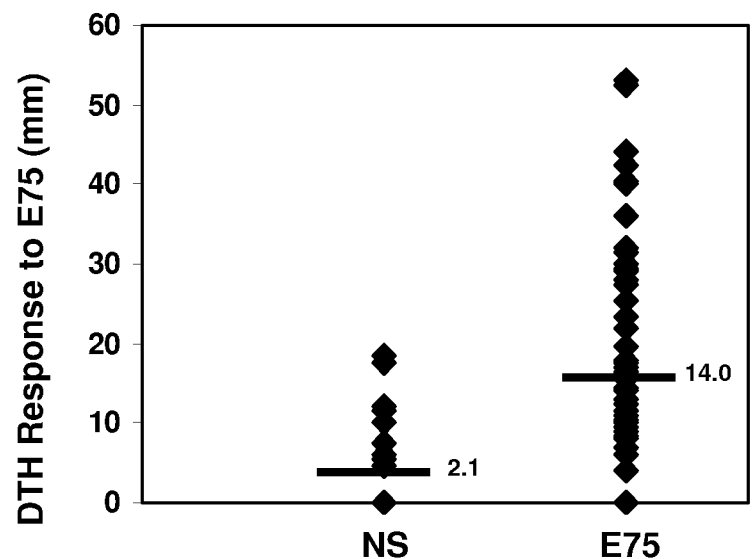
FIGS. 4A to 4D show the results of delayed type hypersensitivity test. (A) DTH for all patients post-vaccination. Control 2.1±0.5 mm compared to peptide 14.0±1.4 mm, P<0.0001. (B) Pre- and post-vaccine DTH for NN patients. There was no difference in saline control vs. peptide pre-vaccination. Post-vaccination, there was a significant increase in DTH response to E75 peptide as compared to post-vaccine control (P<0.001) and compared to pre-vaccination E75 DTH (P<0.001). (C) Post-vaccination DTH by trial. NP patients had significantly larger DTH responses as compared to NN patients (17.3±2.4 mm vs. 10.9±1.5 mm, P=0.02). This can be due to a difference in the median total vaccine dose in the NN group (2000 µg vs. 4000 µg, P<0.0001). (D) Post-vaccination DTH by dose groups. Patients receiving <6000 µg E75 had significantly smaller DTH responses compared to patients receiving a total of 6000 µg. (13.3±1.9 mm vs. 25.1±4.0 mm, P=0.008).

To measure the vaccine's in vivo effectiveness, a post-vaccine DTH was measured one month after vaccine series completion with 100 μg of E75 injected intradermally with a saline volume control. Among all vaccinated patients, 74% had a positive post-vaccine DTH with an average induration to E75 of 14.0±1.4 mm compared to control 2.1±0.5 mm (P<0.0001) (FIG. 4A).

Figure 4B:
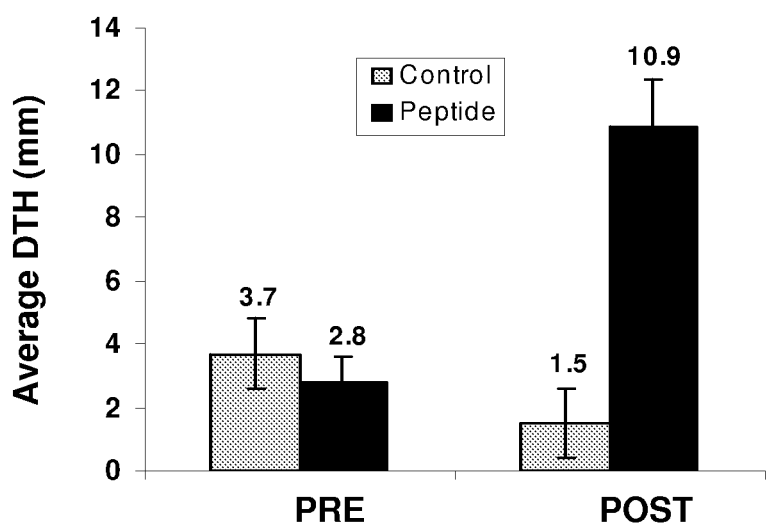

NN patients had a pre-vaccine DTH as well as post-vaccine DTH (FIG. 4B). Pre-vaccination, there was no difference in DTH between E75 and control. Post-vaccination, the DTH response to E75 was statistically larger than control, and the E75 DTH was significantly different post-vaccine compared to pre-vaccine (10.9±1.5 mm vs. 2.8±0.8 mm, P<0.0001).

Figure 4C:
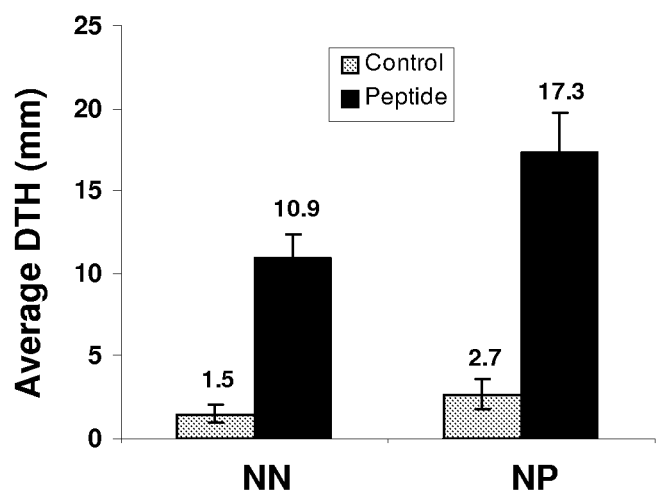
Figure 4D:
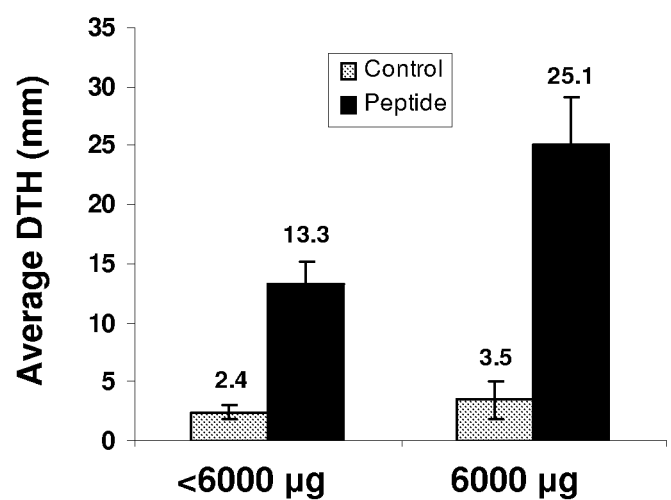

NP patients had a larger post-vaccination E75 DTH response than NN patients (FIG. 4C); a difference likely due to the NN patients receiving much lower amounts of E75 overall. Assessing DTH responses as a function of dose, those patients receiving 6000 μg of E75 had a significantly larger DTH reaction compared with those patients receiving <6000 μg of peptide (25.1±4.0 mm vs. 13.3±1.9 mm, P=0.008) (FIG. 4D).

The HLA-A3⁺ patients had comparable post-vaccination DTH to the HLA-A2⁺ (10.5±2.7 mm vs. 15.1±1.9 mm, P=0.38).

Example 5

HLA-A3⁺ Elispot Assay

Vaccine response for HLA-A3⁺ patients was also assessed by E75-specific interferon-γ ELISPOT. By ELISPOT, the A3 patients demonstrated a range of 0-30 spots/10⁶ cells at baseline that increased to a range of 3-448 spots/10⁶ cells post-vaccination, p=0.04. Most importantly, clinical recurrences were the same in both groups (A3, 9.1% vs A2, 8.2%) and compared to 14.8% in the control group.

Example 6

Breast Cancer Vaccine Booster

Patients. The NP and NN trials were approved at the local Institutional Review Boards and conducted at Walter Reed Army Medical Center (WRAMC), Washington D.C. and the Joyce Murtha Breast Care Center, Windber, Pa. These clinical trials are being conducted under an investigational new drug application (BB-IND #9187) approved by the Food and Drug Administration. All patients had histologically confirmed breast cancer, had completed standard therapy, were disease-free and immunocompetent at time of initial enrollment. HLA-A2⁺ and HLA-A3⁺ patients were vaccinated with varying doses of E75 and GM-CSF and on varying schedules over a six month period, as set forth in the Examples above. Patients were offered an optional booster dose of E75 (1 mg)+GM-CSF (0.250 mg) if they were at least six months from completion of their primary vaccination series.

25 patients received a booster vaccination (Table 3). Just over half (56%) had NP breast cancer. The median time from prior vaccination was 12 months (range 6-24 months). Patients were evaluated as either early booster (EB) patients if they received the booster 6 months after primary series or late booster patients (LB) if they were >6 months from primary series.

TABLE 3

| Patient Demographics. | |
|---|---|
| | Patients (n = 25) |
| Age, median (yrs) | 56 (range 31-76) |
| ≥T2 | 28% |
| Node positive | 56% |
| Grade 3 | 32% |
| ER-PR- | 28% |
| HER2/neu overexpression | 20% |
| Time from primary standard therapy (mos) | 33 (9-200) |
| Time from primary vaccine series (mos) | 12 (6-24) |

Figure 5:
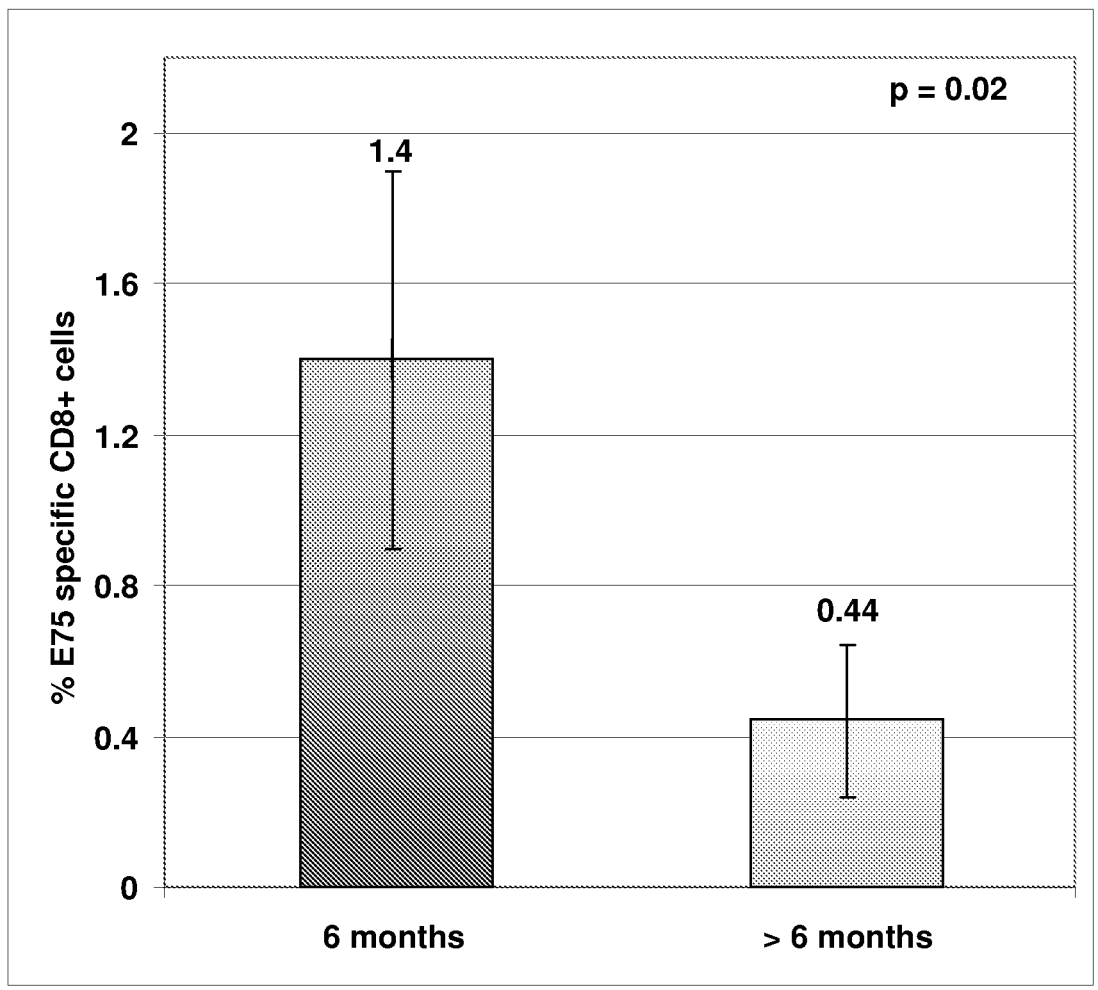
FIG. 5 shows the levels of CD8$^+$ T-cells in booster patients. Patients receiving a booster 6 months after primary vaccination series had significantly higher levels of CD8$^+$ T-cells than patients >6 months from primary vaccination series. Among those patients >6 months, they demonstrated a non-significant decline from 0.7% to 0.44% from their own levels at 6 months post-primary vaccination.

Residual E75-specific immunity declined over time as measured by HLA-A2:IgG dimer. The median level of CD8+ T-cells in EB group (n=6) was 1.4% (0.61-3.43% range) compared to the LB group (n=13) (0.44%, 0-2.67%, p=0.02). For the LB patients, their median dimer level 6 months after the initial series was 0.70% (0.19%-1.55%). This was not statistically different from EB patients' 6 month dimer levels (FIG. 5).

Booster Vaccine.

The E75 peptide was commercially produced in good manufacturing practices grade by NeoMPS (San Diego, Calif.). Peptide purity was verified by high-performance liquid chromatography and mass spectrometry, and the amino acid content was determined by amino acid analysis. The peptide was purified to more than 95%. Sterility and general safety testing was carried out by the manufacturer. Lyophilized peptide was reconstituted in sterile saline at a concentration of 1000 µg in 0.5 mL. The peptide was mixed with GM-CSF (Berlex, Seattle, Wash.) in 0.5 mL, and the 1.0 mL inoculation was split and given intradermally at two sites 5 cm apart. Booster vaccination was given in the same extremity as the primary series.

Toxicity.

Patients were observed 1 hour post vaccination for immediate hypersensitivity reactions. Toxicities were graded by the NCI Common Toxicity Criteria for Adverse Events, v3.0 and reported on a scale from 0 to 5. Patients who had previously had significant (grade 2 or 3) local or systemic toxicity received a reduced dose of GM-CSF at 0.125 mg.

Figure 6:
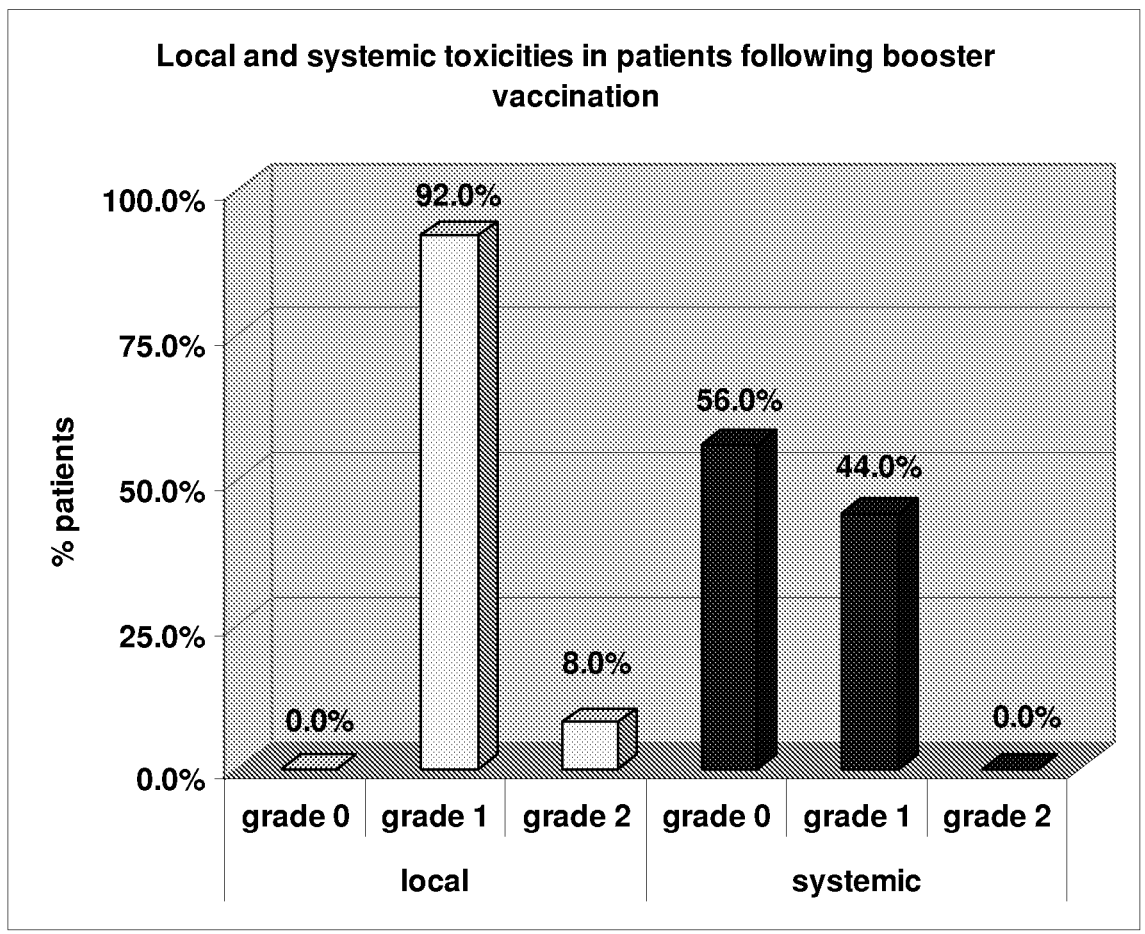
FIG. 6 shows graded local and systemic toxicity. The majority of patients experienced grade 1 local toxicity with only 2 patients experiencing grade 2 local toxicity. Over half of the patients had no systemic toxicity and there were no grade 2 or 3 systemic toxicities. The eleven patients who experienced grade 1 systemic toxicity included (number of instances): fatigue (4), headache (4), myalgias (3), chills (2), fever (2), diarrhea (1), malaise (1), bone pain (1), and arthralgias (1).

The booster dose was very well tolerated (FIG. 6) with primarily grade 1 local toxicity (a desired effect). Over half of the patients had no systemic complaints. There were no grade 3 or 4 toxicities. Only 1 patient (4%) had a higher grade toxicity during the booster than during the primary series (grade 2 local inflammation).

Peripheral Blood Mononuclear Cell Isolation and Cultures.

Blood was drawn before booster vaccination, and 3 to 4 weeks following booster administration to isolate peripheral blood mononuclear cells in Vacutainer CPT tubes, and used as a source of lymphocytes.

HLA-A2:Immunoglobulin Dimer Assay.

The presence of CD8+ E75-specific cells in freshly isolated PBMCs from patients was directly assessed by using the dimer assay described in Example 3 above. Briefly, the HLA-A2:immunoglobulin (Ig) dimer (Pharmingen, San Diego, Calif.) was loaded with the E75 or control peptide (folate binding protein peptide-E37 (25-33) RIAWARTEL (SEQ ID NO:5)) by incubating 1 µg of dimer with an excess (5 µg) of peptide and 0.5 µg of β2-microglobulin (Sigma Chemical Co, St Louis, Mo.) at 37° C. overnight then stored at 4° C. until used. PBMC were washed and re-suspended in PharMingen Stain Buffer (Pharmingen, San Diego, Calif.) and were added at $5 \times 10^5$ cells/100 µl/tube in 5 ml round-bottom polystyrene tubes (Becton Dickinson, Mountain View, Calif.) and stained with the loaded dimers and antibodies. In each HLA-A2+ patient, the level of CD8+ E75-specific cells was determined before and after the vaccine booster.

Figure 7:
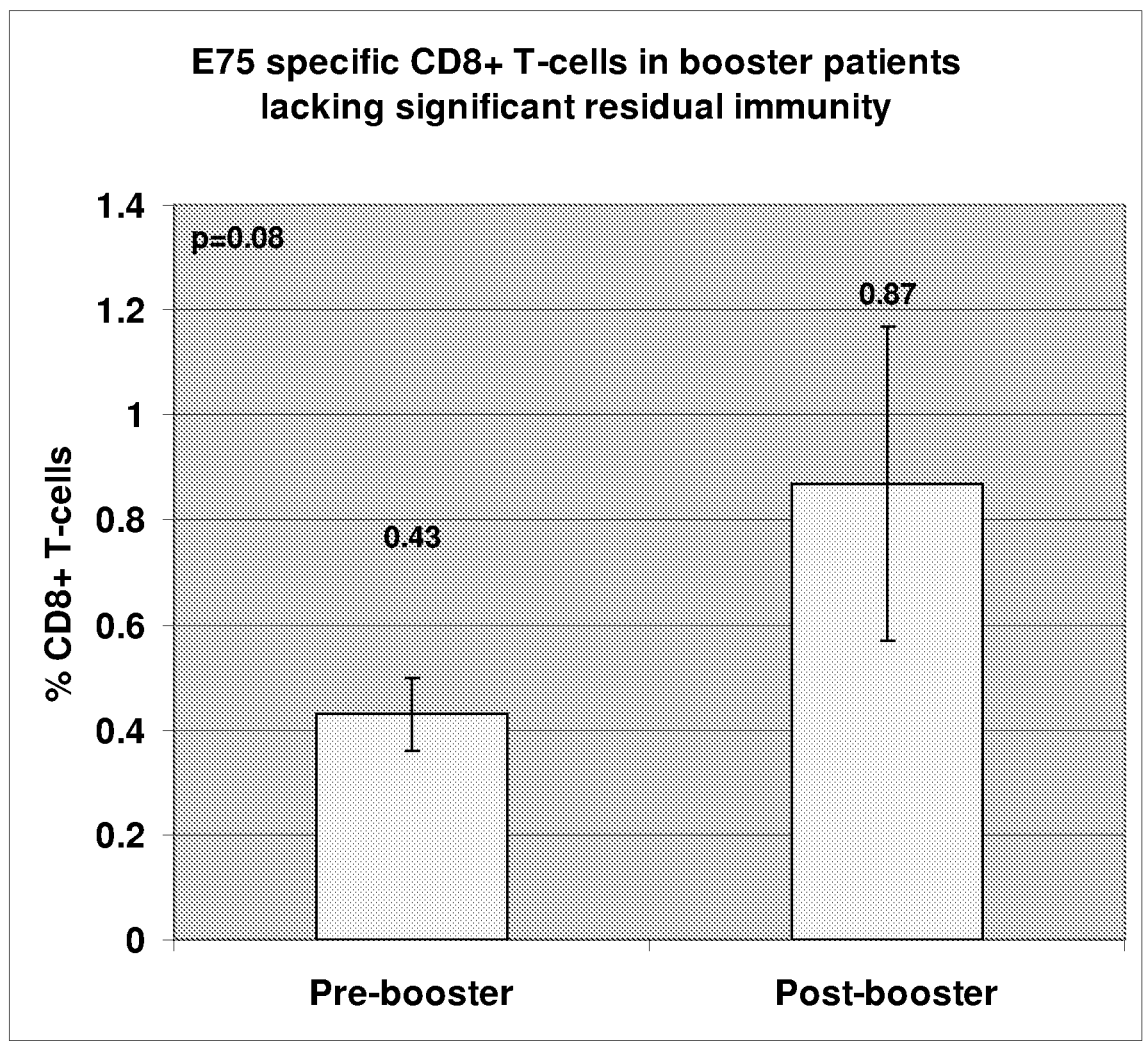
FIG. 7 shows the booster response in patients lacking SRI showed a trend towards an increasing number of antigen specific CD8$^+$ T-cells.

Antigen specific CD8+ T-cells were quantified before and 3-4 weeks after booster vaccination. Significant residual immunity (SRI, defined as antigen specific CD8+ T-cells ≥0.5%) was significantly different in the two groups at 100% (6/6) in the EB patients compared to 30.8% (4/13) of LB patients (p=0.01). Among those patients lacking SRI (n=8) there was a trend towards increased E75-specific CD8+ T-cells (FIG. 7) from 0.43% (0-0.49%) to 0.87% (0-2.3%; p=0.08).

Enzyme-Linked Immunospot Assay.

IFN-γ producing cells were detected using the BD ELISPOT kit either immediately (ex vivo) or after 7-day incubation with peptides. Fresh PBMC were plated into the ELISPOT plate at a concentration of $5 \times 10^5$ cells (ex vivo) or $1 \times 10^5$ (7-day) per well in medium containing IL-7 (ex vivo) or in medium with and without IL-7 (7-day). Cells were stimulated for 16 hours (ex vivo) or 7 days in the presence or absence of peptides (E37, FluM, E75, GP2, HER2/neu 1 µg or 5 µg). Additional incubations in the 7-day wells included combination of E75+ HER2/neu 1 µg or 5 µg. A total of 16 assays were performed on each blood sample, provided enough cells were available. At the end of incubation, the plates were developed as per manufacturer's instructions. A biotinylated detection antibody was added, and the plates incubated overnight at 4° C. Following incubation, the plates were washed, Avidin-HRP solution was added for 1 hour, and spots developed using AEC substrate solution. Spots were counted using the Immunospot Series 2 analyzer and ImmunoSpot software.

Figure 8:
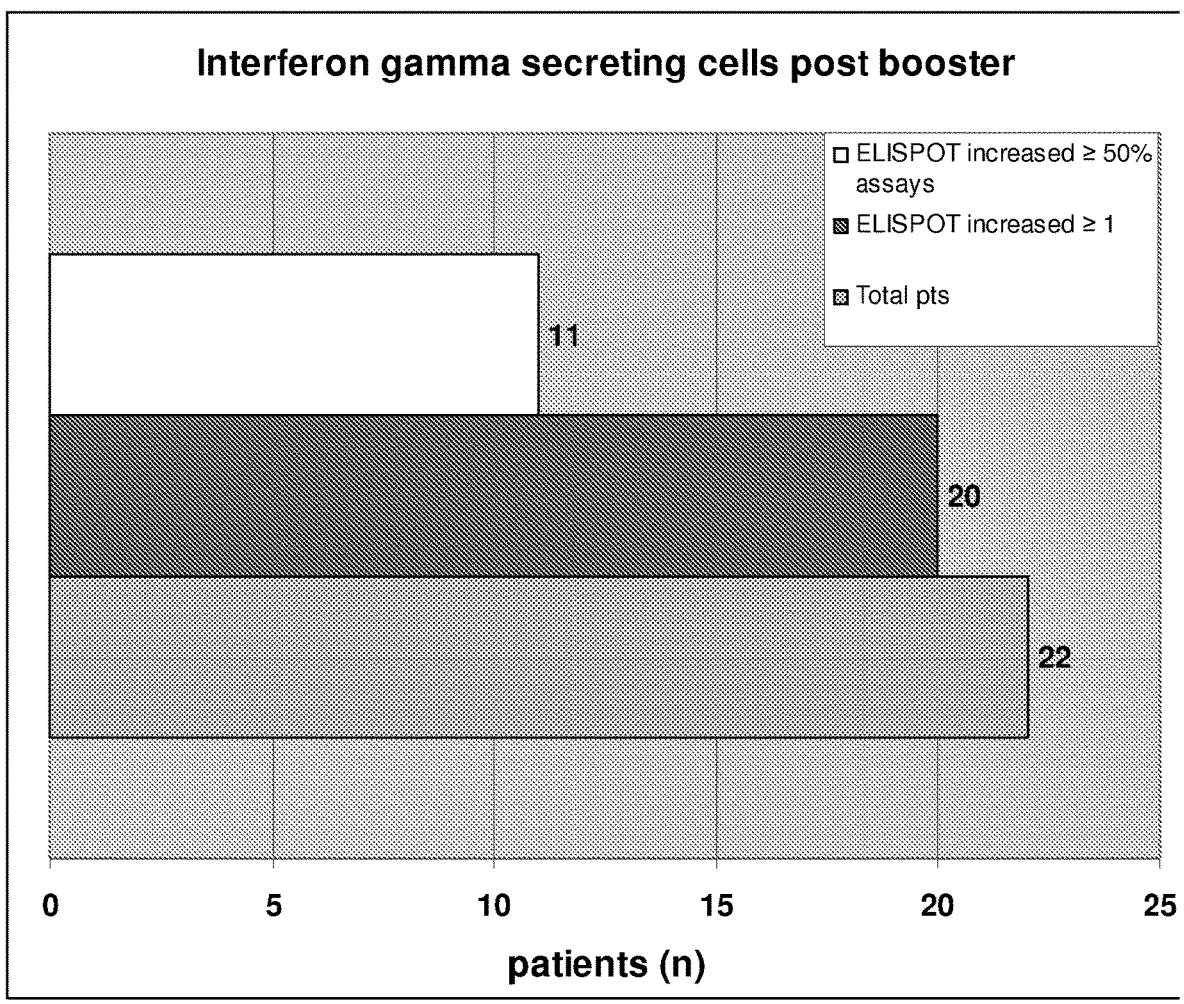
FIG. 8 shows patients demonstrating increased IFN-γ secreting cells detected by enzyme-linked immunoabsorbance. Overall, 91% of patients showed increased antigen-specific (functional) T-cells as measured by ELISPOT, with 50% showing a definite increase (increased IFN-γ secreting cells on ≥50% of assays).

All patients had IFN-γ producing cells quantified before and after booster vaccination in up to 16 different assays, depending on availability of PBMC from a single blood draw. Twenty two patients had at least one paired pre- and post-booster ELISPOT assay (median 10 assays per patient, range 1-14). Among these patients, there were 255 total assays pre-booster, of which 54.5% showed detectable IFN-γ producing. Among 194 paired assays (pre- and post-booster samples from same patient run with same peptide concentration), 78 (40.2%) showed increased IFN-γ producing cells with booster. In all, 20/22 (91%) of patients showed increased IFN-γ producing cells in at least one assay and 11 (50%) showed increased IFN-γ producing cells in at least 50% of the assays. Results are shown in FIG. 8.

Local Reactions.

Local reactions (LR) were measured as an in vivo functional assessment of response. LR were measured 48-72 hours post-vaccination and measured in two directions and reported as an orthogonal mean±SE using the sensitive ball point method. LR were compared to the patient's own previous LR to assess response to booster.

Figure 9:
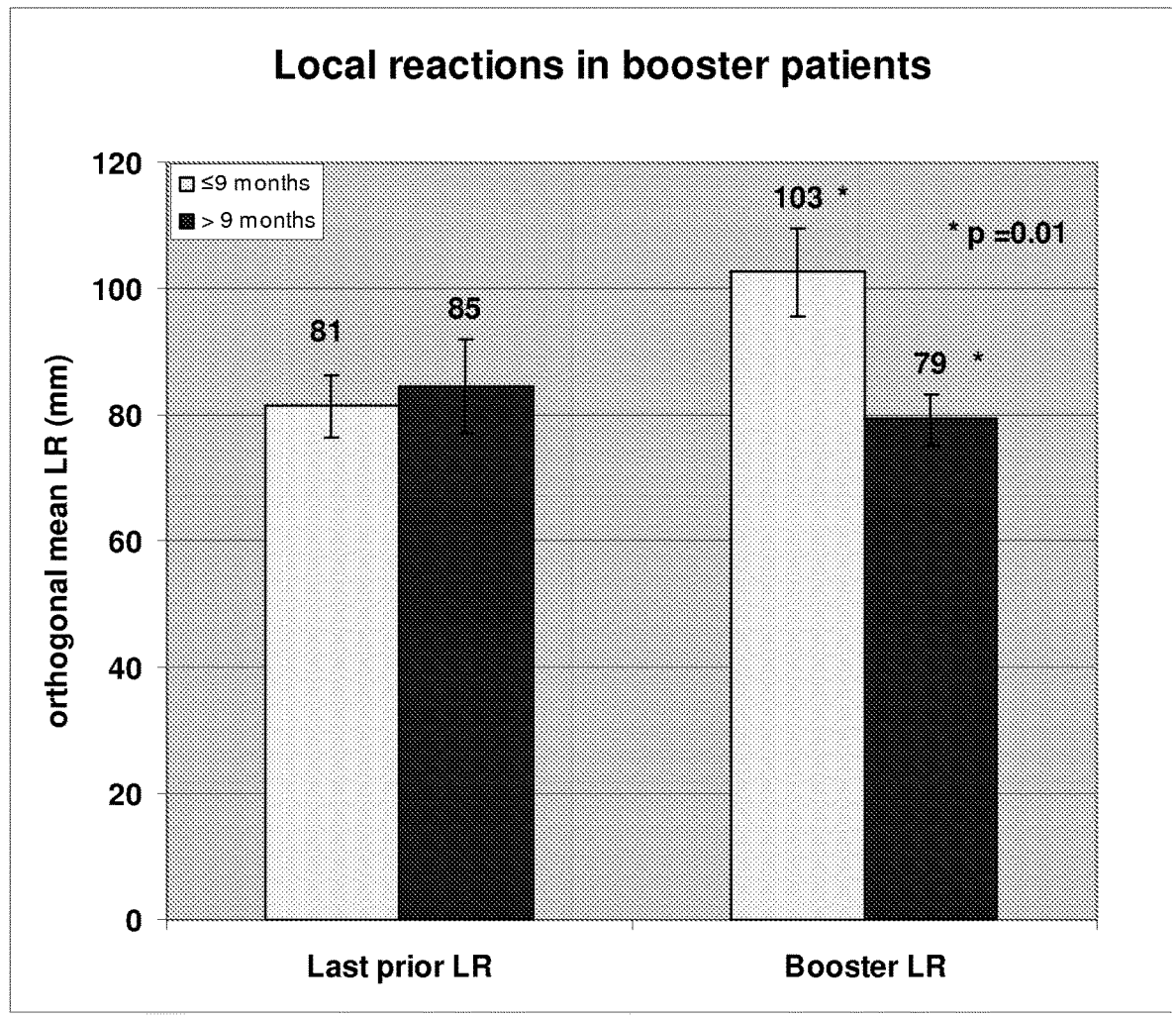
FIG. 9 shows local reactions in booster patients. Patients receiving the booster temporally closer to finishing their primary vaccination series (≤9 months; light bars) had significantly larger LR than those patients >9 months from their primary vaccination series. The two groups had similar LR at the end of the primary series (left side). These data suggest an additive effect of the booster in patients receiving booster sooner and a maintenance effect for patients receiving the booster later.
Figure 10:
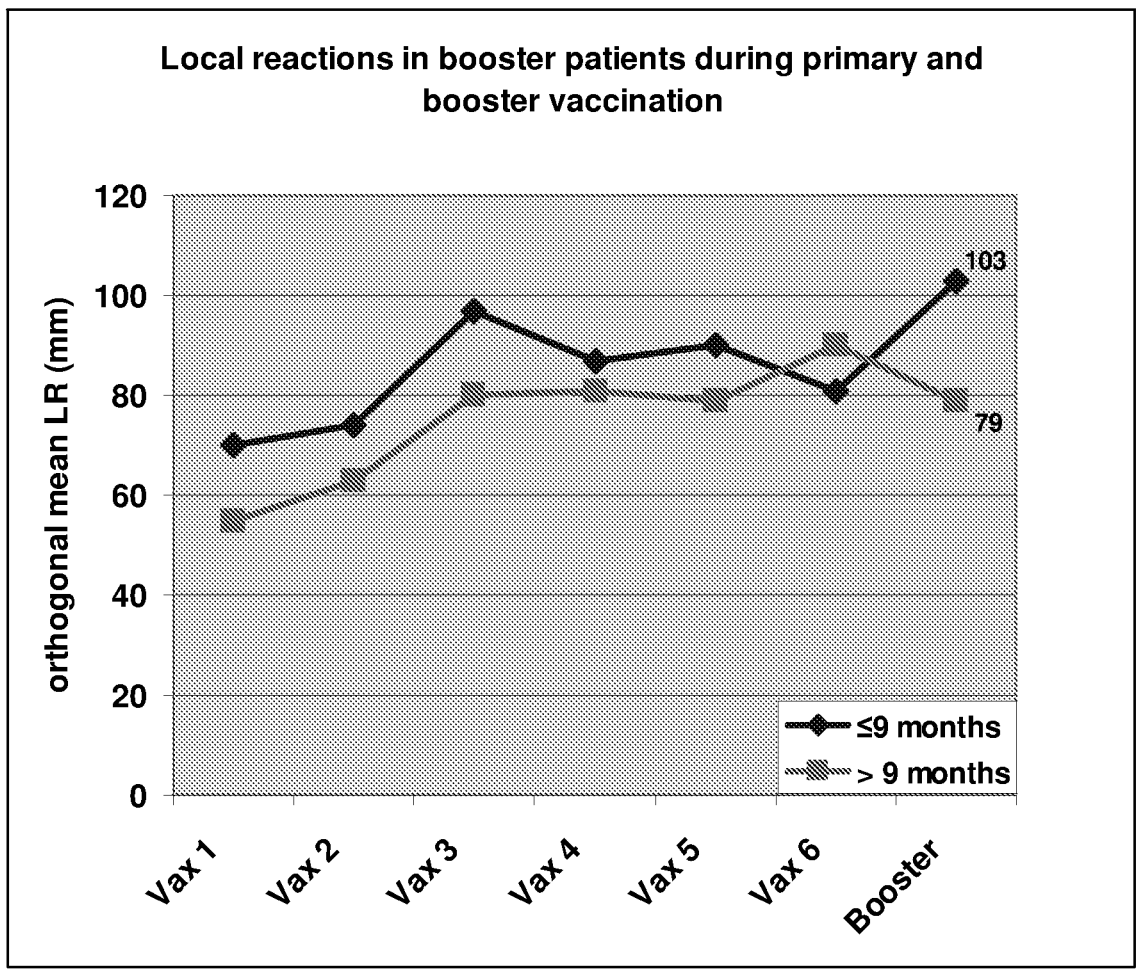
FIG. 10 shows the increasing LR over course of primary series, and illustrates that the two groups were the same in initial series and that the only difference is time from primary series. The vax 6 number is different from Last prior LR number shown in FIG. 7 because some patients only received 4 inoculations. The two groups were statistically identical at all points except vaccine 3 when the ≤9 month group was larger (97 vs. 80, p=0.04).

Patients who received the booster ≤9 months (n=12) from their primary series had significantly larger LR (103±7 mm) than patients >9 months (n=13) from primary series (79±4 mm, p=0.01). There was no difference in the two groups when comparing them at the end of the primary series (<9 months 81±5 mm; >9 months 85±8 mm, p=0.73). Results are shown in FIGS. 9 and 10.

Statistical Analysis.

HLA:IgG dimer values are reported as medians and P values were calculated using the Wilcoxon test. For proportional comparisons, Fisher's exact test was used. Comparison of local reactions was made with paired or unpaired Student's t-test, as appropriate.

Example 7

HER2/Neu (E75) Peptide Vaccine Response Per HER2/Neu Expression Level

Clinical trials were conducted with the HER2/neu E75-peptide vaccine in node-positive and node-negative BCa patients. These patients consist of all levels of HER2/neu expression. Determining HER2/neu status is performed predominately via two tests, immunohistochemistry (IHC) and fluorescence in situ hybridization (FISH). IHC detects over-expression of HER2/neu protein and is reported on a semi-quantitative scale of 0 to 3+(0=negative, 1+=low expression, 2+=intermediate, and 3+=over-expression). FISH on the other hand detects amplification (excess copies) of the HER2/neu gene and is expressed as a ratio of HER2/neu to chromosome 17 and interpreted as over-expression if FISH is >2.0 copies. Concurrence rate of IHC and FISH is approximately 90%.

Materials and Methods:

A subset analysis was performed of 163 BCa patients enrolled in our phase II E75 vaccine trials based on level of HER2/neu expression. Patients were assessed low-expressors (LE=IHC 1+-2+ and FISH>0 but <2.0) vs. over-expressors (OE=IHC 3+ and/or FISH >2.0), and by IHC status (0, 1+, 2+, 3+). Analysis was performed of standard clinocopathologic factors, immunologic response to the vaccine (in vivo DTH reactions and in vitro HLA-A2:IgG dimer assay), and clinical responses (absolute recurrence and mortality rates).

Patient Characteristics and Clinical Protocols:

The E75 NP and NN trials were approved by the Institutional Review Boards and conducted at Walter Reed Army Medical Center, Washington, D.C. and the Joyce Murtha Breast Care Center, Windber, Pa. under investigational new drug application (BB-IND #9187). All patients had histologically confirmed BCa, and had completed a standard course of surgery, chemotherapy, and radiation (as required) before enrollment. Patients on hormonal therapy were continued on their regimen. After proper counseling and consenting, BCa patients were enrolled to the appropriate trial (NP or NN) and HLA typed since E75 binds primarily HLA-A2 found in approximately 40-50% of the general population. HLA-A2+ patients were vaccinated, and HLA-A2− patients were observed prospectively for clinical recurrence. Subsequently HLA-A3+ patients were vaccinated. Before vaccination, patients were skin tested with a panel of recall antigens (Mantoux test). Patients were considered immunocompetent if they reacted (>5 mm) to >2 antigens.

Vaccine:

The E75 peptide was commercially produced in good manufacturing practices grade by NeoMPS, Inc. (San Diego, Calif.). Peptide purity (>95%) was verified by high-performance liquid chromatography and mass spectrometry. Sterility and general safety testing was carried out by the manufacturer. Lyophilized peptide was reconstituted in 0.5 ml sterile saline at 100 mcg, 500 mcg, or 1000 mcg. The peptide was mixed with GM-CSF (Berlex, Seattle, Wash.) in 0.5 ml. The 1.0 ml inoculation was split and given intradermally at two sites 5 cm apart in the same extremity.

Vaccination Series:

The NP trial was designed as a two stage safety trial with escalating doses of peptide in the initial stage and alterations of schedule in the latter stage. Details of the vaccine series have been previously published. Briefly, 3-6 patients were each assigned to receive four or six monthly injections of 100 mcg, 500 mcg, or 1000 mcg of E75 peptide (100:6, 500:4, 500:6, 1000:4 and 1000:6, respectively). Groups were ultimately expanded in order to determine and confirm optimal dosing in NP patients, accounting for the larger number of patients in the latter dose groups.

The NN trial was designed to further delineate optimal biologic dose by varying the dose of GM-CSF and altering the inoculation schedule. Twelve patients with HER2/neu IHC 0 tumors were allowed in this trial to determine the feasibility of vaccinating a presumably antigen-naïve host. Ten patients were assigned to each dose group with constant E75 peptide of 500 mcg to receive three, four, or six monthly injections with varying GM-CSF doses (125 mcg or 250 mcg).

Toxicity:

Patients were observed one hour post-vaccination for immediate hypersensitivity and returned 48-72 hours later to have their injection sites measured and questioned about toxicities. Toxicities were graded by the NCI Common Terminology Criteria for Adverse Events v3.0 (reported on 0-5 scale). Progression from one dose group to the next occurred only if no significant toxicity occurred in the lower dose group. Patient-specific results are reported based on maximal local and systemic toxicity occurring during the series.

Peripheral Blood Mononuclear Cell (PBMC) Isolation and Cultures:

Blood was drawn before each vaccination and at one (post-vaccine) and six months (long-term) after vaccine series completion. 50 ml of blood was drawn and PBMCs isolated. PBMCs were washed and re-suspended in culture medium and used as a source of lymphocytes as previously described.

HLA-A2:Immunoglobulin Dimer Assay:

The presence of CD8+E75-specific cells in freshly isolated PBMCs from patients was directly assessed by using the dimer assay as previously described. Briefly, the HLA-A2:immunoglobulin (Ig) dimer (PharMingen, San Diego, Calif.) was loaded with the E75 or control peptide (E37, folate binding protein (25-33) RIAWARTEL (SEQ ID NO:5)) by incubating 1 mcg of dimer with an excess (5 mcg) of peptide and 0.5 mcg of β2-microglobulin (Sigma, St. Louis, Mo.) at 37° C. overnight then stored at 4° C. until used. PBMCs were washed and re-suspended in PharMingen Stain Buffer (PharMingen) and added at 5×105 cells/100µ tube in 5 ml round-bottom polystyrene tubes (Becton Dickinson, Mountain View, Calif.) and stained with the loaded dimers and antibodies. In each patient the level of CD8+E75-specific cells was determined in response to each successive vaccination, and average post-inoculation levels were compared to their pre-inoculation levels.

Delayed Type Hypersensitivity (DTH):

In both trials, a DTH reaction was assessed with 100 mcg of E75 peptide in 0.5 ml of normal saline (without GM-CSF) and 0.5 ml normal saline as a volume control one month after completion of the vaccine series as described previously. The DTH reaction was measured in two dimensions at 48-72 hours by using the sensitive ballpoint-pen method and reported as the orthogonal mean and compared to control. In the NN trial, a DTH was also performed pre-vaccination as well.

Clinical Recurrences:

All patients were observed for clinical recurrence per standard of care cancer screening as dictated by the patient's primary oncologist. A patient was considered recurrent if biopsy proven or if treated for recurrence by the primary oncology team.

Statistical Analysis:

Recurrence rates were compared between groups using survival analysis by the Kaplan-Meier method, and the proportion of subjects who had recurrences compared using log-ranked analysis. P values for clinico-pathologic factors were calculated using Wilcoxon, Fisher's exact test or $\chi 2$ as appropriate. P values for comparing pre- and post-vaccine dimer levels and DTH were calculated using paired or unpaired two-tailed Student t-test.

Results:

LE (control=44, vaccine=56) vs. OE patients (control=22, vaccine=29) and IHC status control and vaccine groups (0=5 vs. 7, 1+15 vs. 25, 2+24 vs. 26, 3+13 vs. 19 respectively) were assessed. Both LE vs. OE and all IHC status vaccinated groups responded immunologically; however LE patients, and more specifically IHC 1+ patients, had increased long-term in vitro immune response (p=0.04 and p=0.08 respectively). In addition, LE patients trended towards, and IHC 1+ patients had, decreased mortality compared to their control groups (p=0.08 and p=0.04 respectively).

Patients: 186 patients were enrolled in the E75 vaccine studies; 9 withdrew (4 control patients and 5 vaccinated patients—none withdrew due to toxicity) resulting in 177 completing the trials. All control (C) and vaccinated (V) patients in the NP trial (C=46, V=45, total=91 patients) had IHC, FISH, or both tests performed. In the NN trial (C=35, V=51, total=86 patients) 12 patients had HER2/neu IHC 0 tumors (C=5, V=7). Also in the NN trial, 14 patient's (C=7, V=7) tumors did not undergo IHC or FISH—these 14 patients have been excluded from subset analysis; therefore 163 patients were available for analysis.

LE vs. OE Subset Analysis:

Patients per Expression: Subset analysis was performed comparing LE (IHC 1+-2+ or FISH >0 and <2.0) vs. OE (IHC 3+ or FISH >2.0). Sixty-six patients in the control group had IHC or FISH performed (LE=44, OE=22). A total of 85 patients in the E75 vaccine group had IHC or FISH performed (LE=56, OE=29). A comparable number of C and V patients were in the LE (67% vs. 66% respectively) and OE groups (33% vs. 34% respectively).

Demographics, prognostic factors, and treatment profiles of LE vs. OE patients are presented in Table 4. In regards to LE patients no statistical differences were noted between C and V patients. With OE patients, a statistically larger number of V patients were hormone receptor negative than in the C group (p=0.02) (Table 4).

TABLE 4

Demographics, prognostic factors, and treatment profiles of patients enrolled in E75 Phase II trial by LE vs. OE.

|  | LE Control (n = 44) | LE Vaccine (n = 56) | P | OE Control (n = 22) | OE Vaccine (n = 29) | P |
|---|---|---|---|---|---|---|
| Median age, years | 55 | 56 |  | 50 | 52 |  |
| Range years | 31-82 | 27-77 | 0.7 | 32-75 | 37-68 | 0.1 |
| Race |  |  |  |  |  |  |
| White, % | 86.4% | 89.3% | 0.8 | 72.7% | 86.2% | 0.3 |
| Other, % | 13.6% | 10.7% | 0.8 | 27.3% | 13.8% | 0.3 |
| Tumor size |  |  |  |  |  |  |
| T2-T4, % | 38.6% | 33.9% | 0.7 | 31.8% | 34.5% | 0.9 |
| Histological grade |  |  |  |  |  |  |
| Grade III, % | 27.2% | 30.4% | 0.8 | 63.6% | 62.1% | 0.9 |
| Node Positive (NP), % | 54.5% | 58.9% | 0.7 | 90.1% | 55.2% | 0.06 |
| Hormone receptor-, % | 15.9% | 19.6% | 0.8 | 27.3% | 62.1% | 0.02* |
| Chemotherapy, % | 72.7% | 75.0% | 0.8 | 86.4% | 96.6% | 0.3 |
| XRT, % | 84.1% | 75.0% | 0.3 | 72.7% | 75.9% | NS |
| Hormonal therapy, % | 81.8% | 76.8% | 0.6 | 63.6% | 41.4% | 0.2 |
| Herceptin, % | 0.2% | 0.2% | NS | 9.1% | 24.1% | 0.3 |

*Statistically significant difference.

Figure 11A:
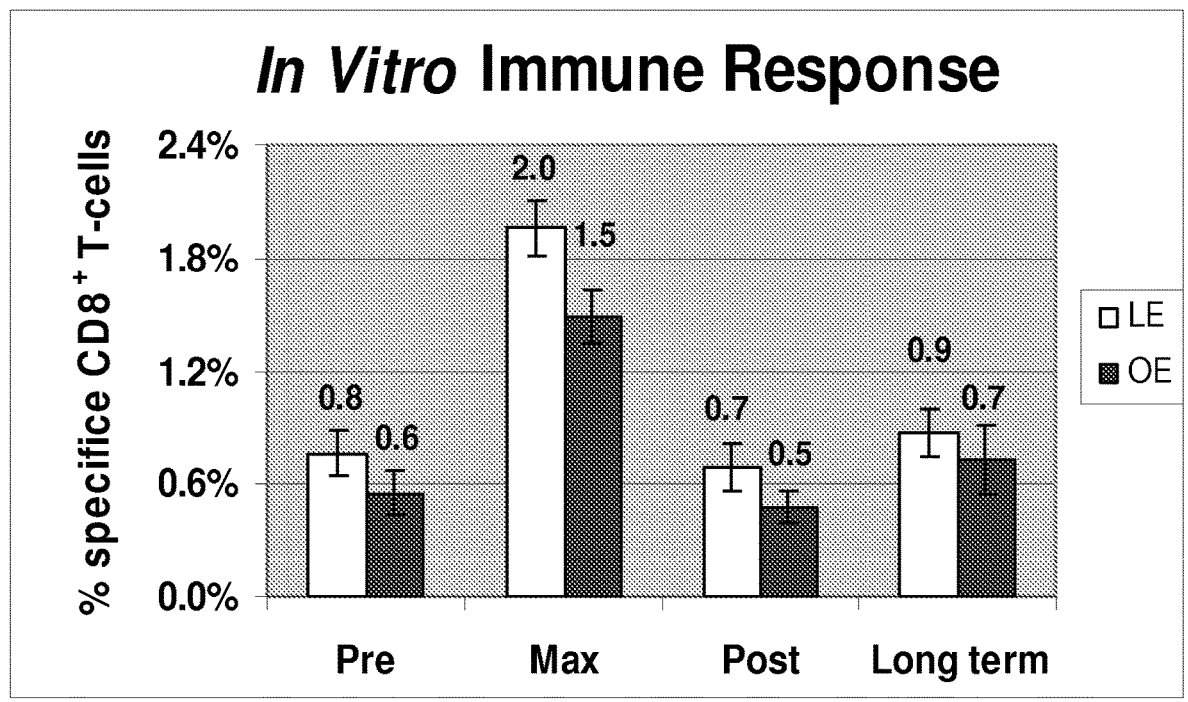
FIG. 11A to FIG. 11D show immunologic (mean±SE) and clinical responses (absolute recurrence and mortality rates) of patients enrolled in E75 Phase II trial by HER2/neu LE vs. OE.

Immunologic Response per Expression:

The E75 vaccine was capable of eliciting an in vitro immune response in both the LE and OE patients. Significant increases from pre-vaccine to max E75-specific CD8+ T cells was noted in both groups (LE p<0.001, OE p<0.001). LE patients had statistically higher maximum immune response compared to OE patients (p=0.04) (FIG. 11A).

Figure 11B:
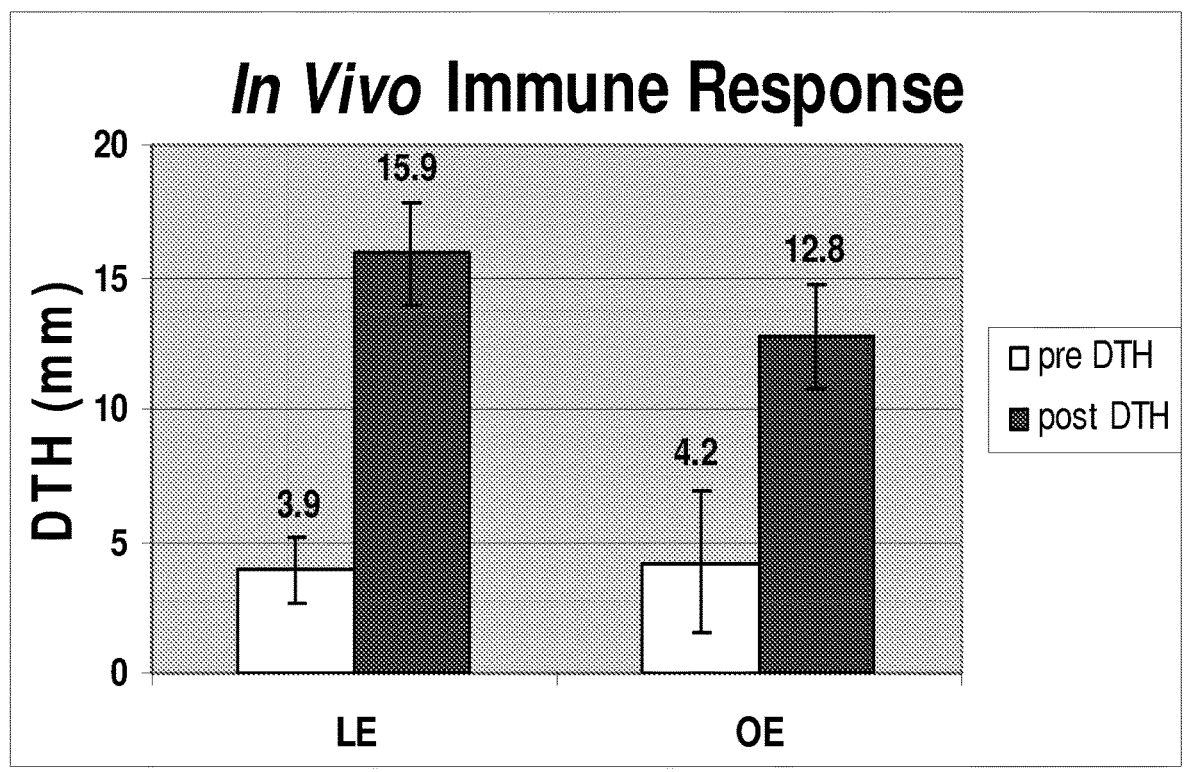

Both LE and OE patients were able to elicit an in vivo immune response as measured via DTH pre and post-vaccine. Significant pre-post DTH increases were noted in both categories (LE p<0.001, OE p=0.02) (FIG. 11B). Although the LE post-DTH is larger than OE post-DTH (15.9+1.9 mm vs. 12.8+2.0 mm, respectively), there is no statistical significance (p=0.5). Overall, the E75 vaccine appears more immunologically active in LE patients.

Figure 11C:
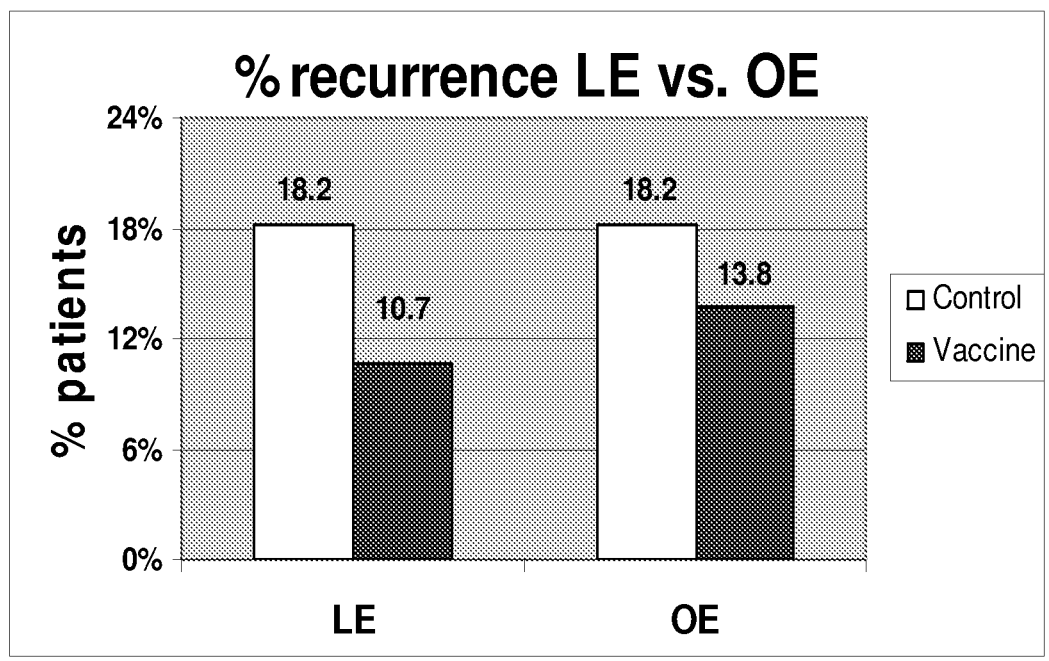
Figure 11D:
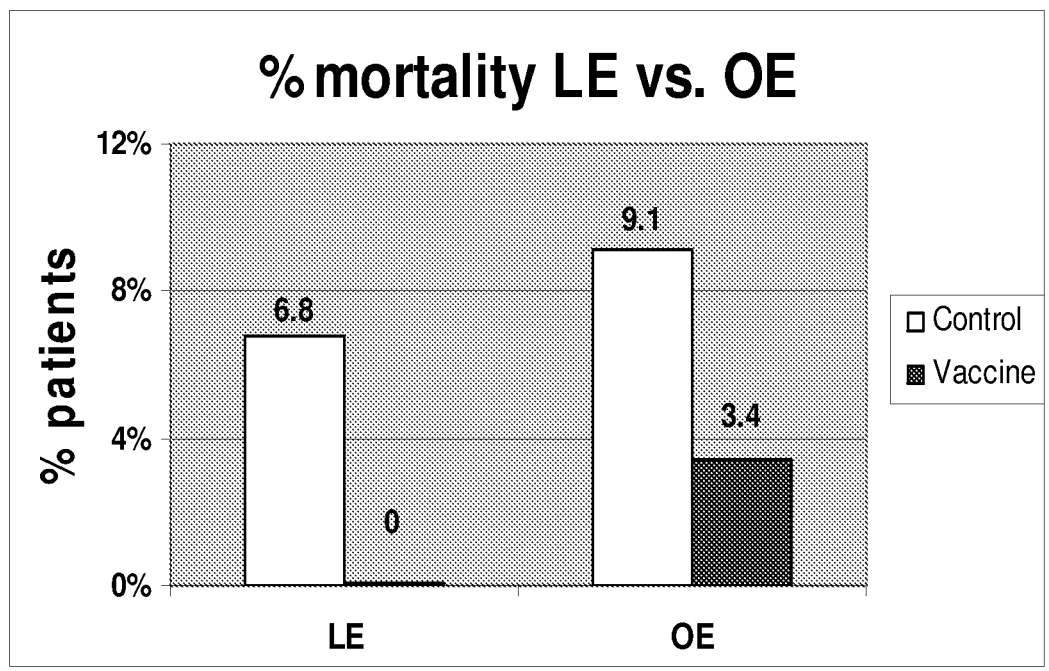

Clinical Response Per Expression:

Clinical response, evaluated by recurrence and mortality, is noted in FIGS. 11C and 11D. All V patients (LE=10.7% vs. OE=13.8%) appeared to have decreased recurrence rates when compared to the C patients (LE & OE=18.2%), but these numbers were not statistically significant. More importantly, there was a trend towards decreased mortality in the V patients, most impressively seen in the LE patients (C=6.8% vs. V=0.0%; p=0.08).

IHC Status Subset Analysis:

Patients per IHC Status:

The C group had 57 patients' pathology specimens that underwent IHC (0=5, 1+=15, 2+=24, 3+=13). The E75 V group had 77 patients' pathology that underwent IHC (0=7, 1+=25, 2+=26, 3+=19). A comparable percentage of C and V patients were in each IHC group (0 C=8.8% vs. V=9.1%; 1+C=26.3% vs. V=32.5%, 2+C=42.1% vs. V=33.8%, 3+C=22.8% vs. V=24.7%).

Demographics, prognostic factors, and treatment profiles per IHC status are presented in Table 5. There were two significant differences in prognostic factors for IHC status groups. IHC 1+ patients had a larger percentage of T2-T4 tumors in the C group compared to the V group (66.7% vs. 30.8%, p=0.05). IHC 3+ C patients were all NP and 42.1% of V patients were NP (p=0.003).

TABLE 5

Demographics, prognostic factors, and treatment profiles of patients enrolled in E75 Phase II trial by HER2/neu experssion level.

|  | 0 Control (n = 5) | 0 Vaccine (n = 7) | p | 1+ Control (n = 15) | 1+ Vaccine (n = 25) | p | 2+ Control (n = 24) | 2+ Vaccine (n = 26) | p | 3+ Control (n = 13) | 3+ Vaccine (n = 19) | p |
|---|---|---|---|---|---|---|---|---|---|---|---|---|
| Median age, years | 50 | 60 |  | 54 | 54 |  | 50 | 57 |  | 49 | 51 |  |
| Range years | 38-74 | 31-74 | 0.4 | 44-82 | 42-71 | 0.4 | 31-75 | 27-77 | 0.2 | 31-74 | 37-62 | 0.2 |
| Race |  |  |  |  |  |  |  |  |  |  |  |  |
| White, % | 100.0% | 71.4% | 0.5 | 73.3% | 84.0% | 0.4 | 87.5% | 92.3% |  | 61.5% | 89.5% | 0.1 |
| Other, % | 0.0% | 28.6% | NS | 26.7% | 16.0% | NS | 12.5% | 7.7% | 0.7 | 40.5% | 10.5% | NS |

TABLE 5-continued

Demographics, prognostic factors, and treatment profiles of patients enrolled in E75 Phase II trial by HER2/neu experssion level.

| | 0 Control (n = 5) | 0 Vaccine (n = 7) | p | 1+ Control (n = 15) | 1+ Vaccine (n = 25) | p | 2+ Control (n = 24) | 2+ Vaccine (n = 26) | p | 3+ Control (n = 13) | 3+ Vaccine (n = 19) | p |
|---|---|---|---|---|---|---|---|---|---|---|---|---|
| Tumor Size | | | | | | | | | | | | |
| T2-T4, % | 40.0% | 14.3% | 0.5 | 66.7% | 28.0% | 0.05* | 29.2% | 46.2% | 0.2 | 38.5% | 36.8% | 0.8 |
| Histological grade | | | | | | | | | | | | |
| Grade III, % | 20.0% | 14.3% | 0.6 | 33.3% | 36.0% | 0.7 | 37.5% | 38.5% | 0.9 | 61.5% | 57.9% | 0.8 |
| Node Positive (NP), % | 0.00% | 0.00% | NS | 80.0% | 60.0% | 0.3 | 79.2% | 80.8% | 0.8 | 100.0% | 42.1% | 0.003* |
| Hormone receptor-, % | 20.0% | 14.3% | 0.6 | 13.3% | 28.0% | 0.4 | 16.7% | 11.5% | 0.9 | 38.5% | 63.2% | 0.2 |
| Chemotherapy, % | 80.0$ | 42.9% | 0.3 | 80.0% | 76.0% | 0.9 | 87.5% | 96.2% | 0.5 | 92.3% | 94.7% | 0.6 |
| XRT, % | 100.0% | 42.9% | 0.08 | 66.7% | 76.0% | 0.7 | 87.5% | 96.2% | 0.5 | 69.2% | 94.7% | 0.1 |
| Hormonal Therapy, % | 80.0% | 85.7% | 0.6 | 80.0% | 72.0% | 0.9 | 79.2% | 73.1% | 0.6 | 53.8% | 73.7% | 0.3 |
| Herceptin, % | 0.0% | 0.0% | NS | 0.0% | 0.0% | NS | 8.3% | 7.7% | 0.9 | 7.7% | 10.5% | 0.7 |

*Statistically significant differences.

Figure 12A:
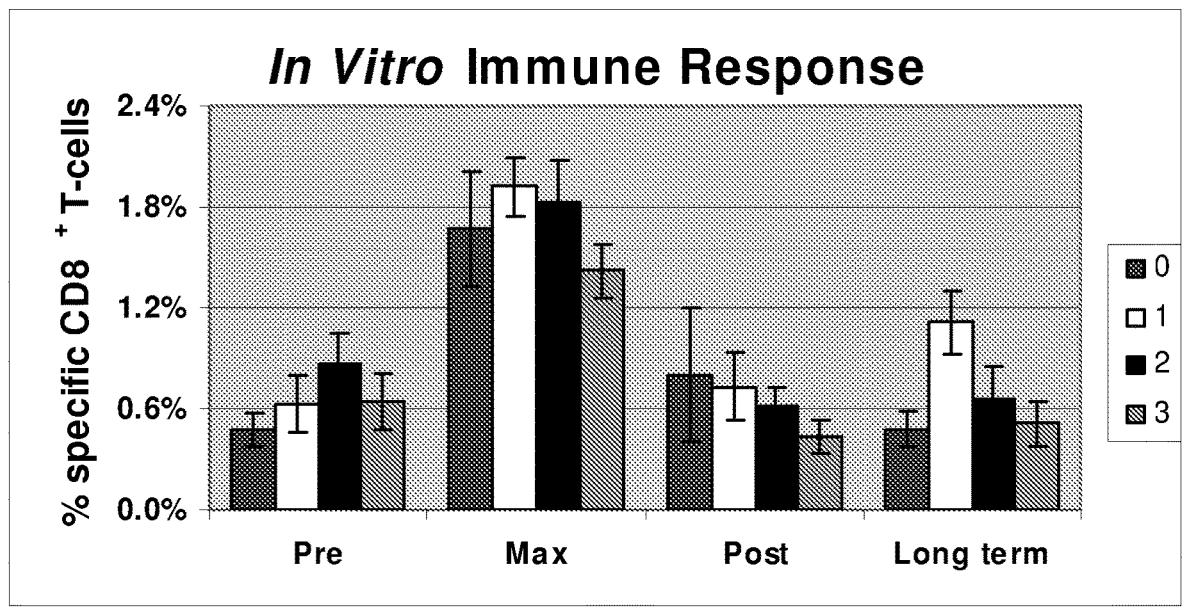

Immunologic Response per IHC Status:

The E75 vaccine was capable of eliciting an in vitro immune response in all IHC categories. All IHC groups (0, 1+, 2+, 3+) responded to the vaccine as noted by significant increases from pre-vaccine to max E75-specific CD8+ T cells (0 p=0.007, 1+p<0.001, 2+p=0.004, 3+p=0.002). Only IHC 1+ patients trended towards significant pre to long-term increase in E75-specific CD8+ T cells (p=0.08) (FIG. 12A).

Figure 12B:
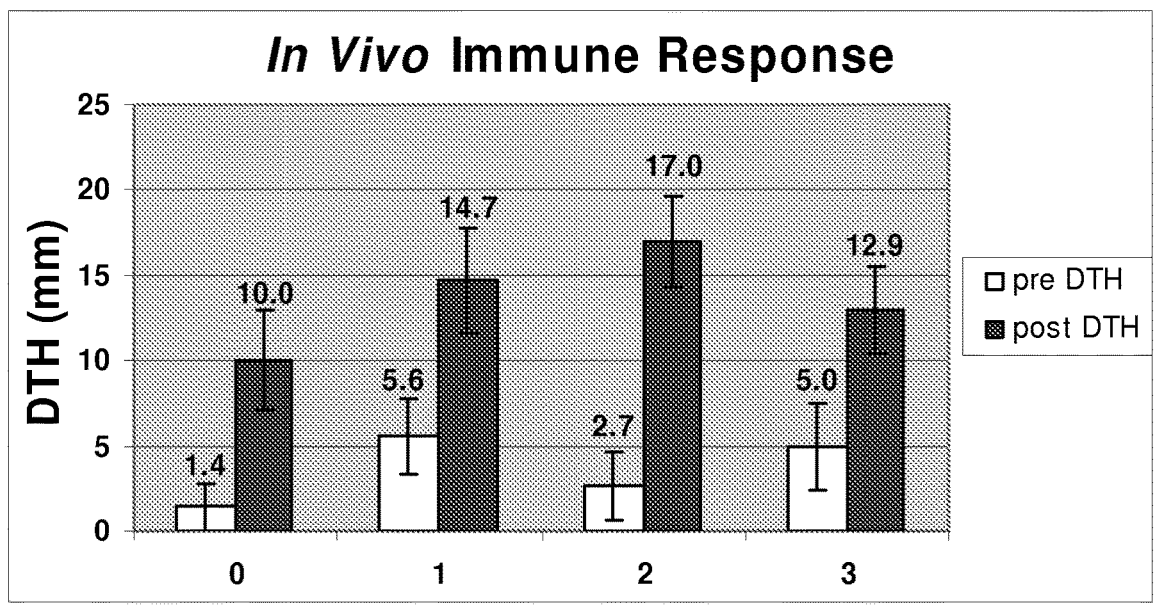

In addition all patients were able to elicit an in vivo immune response as measured via DTH pre- and post-vaccine. Significant pre-post DTH increases were noted in all IHC categories (0 p=0.03, 1+p=0.02, 2+p=0.02, 3+p=0.05). Overall, regardless of HER2/neu expression as measured by IHC, the vaccine was immunologically effective but appears most effective in the IHC 1+ patients (FIG. 12B).

Figure 12C:
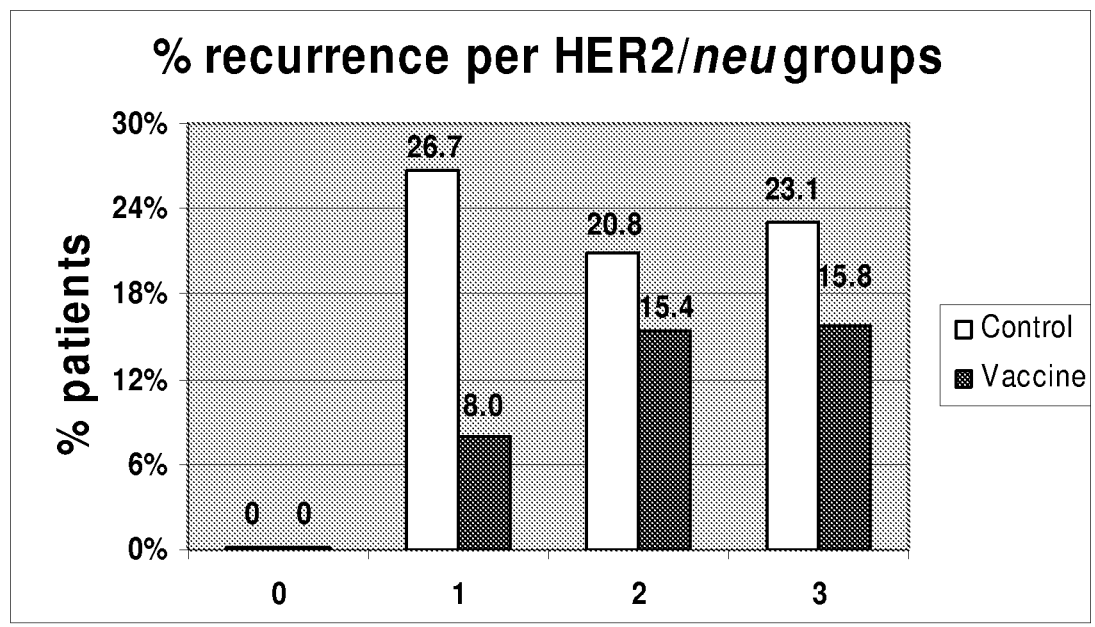
Figure 12D:
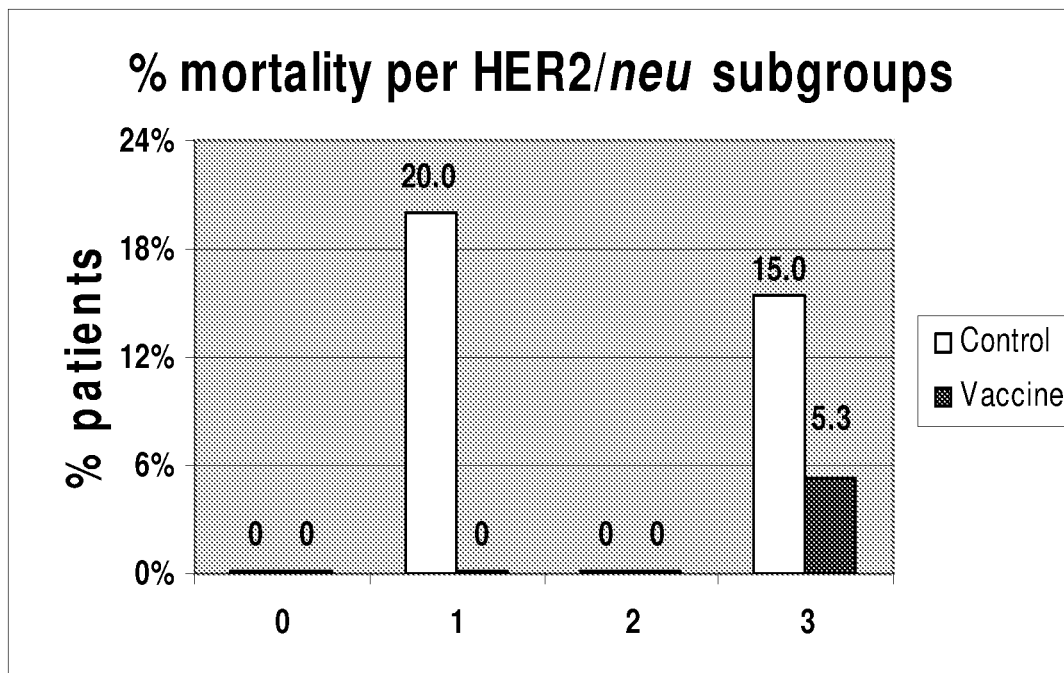

Clinical Response per IHC Status:

Clinical response, evaluated by recurrence and mortality, is noted in FIGS. 12C and 12D. In all IHC categories (except IHC 0 where no patients recurred), there were decreased recurrence rates when comparing C and V patients, although the numbers do not achieve statistical significance. More importantly, there was a significant decrease in mortality in IHC 1+ patients, C=20% and V=0% mortality (p=0.04).

In a previous phase II trial, administration of the E75 vaccine resulted in decreased recurrence rates and a trend towards decreased mortality rates at 20 months, but these differences lost significance as immunity waned without the use of boosters. It was shown that patients having all levels of HER2/neu expression responded immunologically to the vaccine, but that the LE (and specifically IHC 1+) patients had more robust immunologic responses, and derived the greatest clinical benefit with decreased mortality. It was also shown that antigen naïve patients respond immunologically to the vaccine as well.

When ranges are used herein for physical properties, such as molecular weight, or chemical properties, such as chemical formulae, all combinations and subcombinations of ranges specific aspects therein are intended to be included.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

Sequence Listing

```
SEQ ID NO: 1 (HER2/neu amino acid sequence)
MKLRLPASPETHLDMLRHLYQGCQVVQGNLELTYLPTNASLSFL-
QDIQEVQGYVLIAHNQVRQVPLQRLRIVRGTQLFEDNYALAVLDNGDPLN
NTTPVTGASPGGLRELQLRSLTEILKGGVLIQRNPQLCYQDTILWKDIFH
KNNQLALTLIDTNRSRACHPCSPMCKGSRCWGESSEDCQSLTRTVCAGGC
ARCKGPLPTDCCHEQCAAGCTGPKHSDCLACLHFNHSGICELHCPALVTY
NTDTFESMPNPEGRYTFGASCVTACPYNYLSTDVGSCTLVCPLHNQEVTA
EDGTQRCEKCSKPCARVCYGLGMEHLREVRAVTSANIQEFAGCKKIFGSL
AFLPESFDGDPASNTAPLQPEQLQVFETLEEITGYLYISAWPDSLPDLSV
FQNLQVIRGRILHNGAYSLTLQGLGISWLGLRSLRELGSGLALIHHNTHL
CFVHTVPWDQLFRNPHQALLHTANRPEDECVGEGLACHQLCARGHCWGPG
PTQCVNCSQFLRGQECVEECRVLQGLPREYVNARHCLPCHPECQPQNGSV
TCFGPEADQCVACAHYKDPPFCVARCPSGVKPDLSYMPIWKFPDEEGACQ
PCPINCTHSCVDLDDKGCPAEQRASPLTSIISAVVGILLVVVLGVVFGIL
IKRRQQKIRKYTMRRLLQETELVEPLTPSGAMPNQAQMRILKETELRKVK
VLGSGAFGTVYKGIWIPDGENVKIPVAIKVLRENTSPKANKEILDEAYVM
AGVGSPYVSRLLGICLTSTVQLVTQLMPYGCLLDHVRENRGRLGSQDLLN
WCMQIAKGMSYLEDVRLVHRDLAARNVLVKSPNHVKITDFGLARLLDIDE
TEYHADGGKVPIKWMALESILRRRFTHQSDVWSYGVTVWELMTFGAKPYD
GIPAREIPDLLEKGERLPQPPICTIDVYMIMVKCWMIDSECRPRFRELVS
EFSRMARDPQRFVVIQNEDLGPASPLDSTFYRSLLEDDDMGDLVDAEEYL
VPQQGFFCPDPAPGAGGMVHHRHRSSSTRSGGGDLTLGLEPSEEEAPRSP
LAPSEGAGSDVFDGDLGMGAAKGLQSLPTHDPSPLQRYSEDPTVPLPSET
DGYVAPLTCSPQPEYVNQPDVRPQPPSPREGPLPAARPAGATLERPKTLS
PGKNGVVKDVFAFGGAVENPEYLTPQGGAAPQPHPPPAFSPAFDNLYYWD
QDPPERGAPPSTFKGTPTAENPEYLGLDVPV SEQ ID NO: 2 (E75 peptide)
KIFGSLAFL

SEQ ID NO: 3
BIMAS

SEQ ID NO: 4
SYFPEITHI

SEQ ID NO: 5
RIAWARTEL
```

What is claimed:

1. A method of inducing protective or therapeutic immunity against a HER2/neu expressing tumor with a fluorescence in situ hybridization (FISH) rating of greater than about 0 to less than about 2.0 for HER2/neu gene expression in a subject, the method comprising administering to the subject an effective amount of a composition comprising a pharmaceutically effective carrier, a peptide having the amino acid sequence SEQ ID NO:2, and an adjuvant comprising a compound or compounds selected from the group consisting of emulsifiers, muramyl dipeptides, avridine, aluminum hydroxide, chitosan-based adjuvants, saponins, oils, Amphigen, LPS, bacterial cell wall extracts, bacterial DNA, CpG sequences, synthetic oligonucleotides, cytokines and combinations thereof.

2. The method of claim 1, further comprising administering to the subject a booster composition comprising an effective amount of a pharmaceutically effective carrier and a peptide having the amino acid sequence SEQ ID NO:2.

3. The method of claim 1, wherein the subject is a human.

4. The method of claim 1, wherein the HER2/neu expressing tumor has an immunohistochemistry (IHC) rating of 1+ or 2+ for HER2/neu protein expression.

5. The method of claim 2, wherein the booster composition further comprises an adjuvant.

6. The method of claim 3, wherein the human had node positive breast cancer.

7. The method of claim 3, wherein the human had node negative breast cancer.

8. The method of claim 5, wherein the adjuvant comprising a compound or compounds is selected from the group consisting of emulsifiers, muramyl dipeptides, avridine, aluminum hydroxide, chitosan-based adjuvants, saponins, oils, Amphigen, LPS, bacterial cell wall extracts, bacterial DNA, CpG sequences, synthetic oligonucleotides, cytokines and combinations thereof.

9. The method of claim 5, wherein the adjuvant comprises granulocyte macrophage-colony stimulating factor (GM-CSF).

* * * * *